United States Patent
Král et al.

(10) Patent No.: US 8,013,190 B2
(45) Date of Patent: Sep. 6, 2011

(54) CHEMICAL COMPOSITION WITH BORANE CLUSTERS FOR USE AS AN HIV PROTEASE INHIBITOR

(75) Inventors: Vladimír Král, Prague (CZ); Petr Cigler, Ceské Budejovice (CZ); Jan Konvalinka, Prague (CZ); Milan Kozísek, Prague (CZ); Jana Prejdová, Prague (CZ); Bohumír Grüner, Prague (CZ); Jaromír Plesek, Prague (CZ); Martin Lepsík, Prague (CZ); Jana Pokorná, Prague (CZ); Hans-Georg Kräusslich, Heidelberg (DE); Jochen Bodem, Heidelberg (DE)

(73) Assignees: Vysoka Skola Chemicko-Technologicka V Praze, Prague (CZ); Ustav Organicke Chemie A Biochemie AV CZ, Prague (CZ); Ustav Anorganicke Chemie AV CZ, Rez u Prahy (CZ); Department of Virology, University of Heidelberg, Heidelberg (DE)

( * ) Notice: Subject to any disclaimer, the term of this patent is extended or adjusted under 35 U.S.C. 154(b) by 399 days.

(21) Appl. No.: 10/597,408

(22) PCT Filed: Jan. 27, 2005

(86) PCT No.: PCT/CZ2005/000006
§ 371 (c)(1),
(2), (4) Date: Jul. 3, 2007

(87) PCT Pub. No.: WO2005/073240
PCT Pub. Date: Aug. 11, 2005

(65) Prior Publication Data
US 2009/0012044 A1 Jan. 8, 2009

(30) Foreign Application Priority Data

Jan. 29, 2004 (CZ) .................................. 2004-162
Jan. 14, 2005 (CZ) .................................... 2005-27

(51) Int. Cl.
*C07F 5/02* (2006.01)
(52) U.S. Cl. ............................. 568/5; 568/6; 514/64
(58) Field of Classification Search .................. 514/64; 568/5, 6
See application file for complete search history.

(56) References Cited

FOREIGN PATENT DOCUMENTS

JP 07247297 A * 9/1995

OTHER PUBLICATIONS

Pitochelli et al. (J. Am. Chem. Soc., 1960, 82 (12), 3228-3229).*
Sivaev et al. (J. Organometal. Chem. 2002 649, 181-190).*

(Continued)

*Primary Examiner* — Andrew D Kosar
*Assistant Examiner* — Valerie Rodriguez-Garcia
(74) *Attorney, Agent, or Firm* — Egbert Law Offices PLLC

(57) ABSTRACT

The present invention provides novel HIV protease inhibitors containing substituted borane, carborane or metallacarborane clusters with 6 to 12 boron atoms in each cluster. The charge of each borane, carborane or metallacarborane cluster is 0, −1 or −2. The number of borane, carborane or metallacarborane clusters in the inhibitor molecule is 1 to 9, and the carborane clusters in metallacarborane inhibitors are coordinated to transition metal atom, selected from the group containing cobalt, iron, nickel and ruthenium. In the cluster, heteroatoms can be present, such as nitrogen, phosphorus, silicon, germanium, tin and sulphur. The present invention covers pharmaceutical compositions containing these inhibitors and their use, both in vitro and in vivo. They are characterized by high effectiveness and stability.

3 Claims, 19 Drawing Sheets

OTHER PUBLICATIONS

Jordan, V. C. Nature Reviews: Drug Discovery, 2, 2003, pp. 205-213).*

Dörwald, F. Zaragoza. Side Reactions in Organic Synthesis: A Guide to Successful Synthesis Design, Weinheim: WILEY-VCH Verlag GmbH & Co. KGaA, 2005.*

Gruner, B. et al, "Cobalt bis(dicarbollides) (1-) Covalently Attached to the Calix[4]arene Platform: The First Combination of Organic Bowl-Shaped Matrices and Inorganic Metallaborane Cluster", European Journal of Organic Chemistry, May 2005, p. 2022-2039, No. 10.

Gruner, B. et al, "Cobalt bis(dicarbolllide) ions With Covalently Bonded CMPO Groups as Selective Extraction Agents for Lanhanide Actinide Cations from Highly Acidic Nuclear Waste Solutions", New Journal of Chemistry, 2002, pp. 1519-1527, vol. 26, No. 10.

Sivaev, I. et al, "Synthesis of Functional Derivatives of the '3,3'-Co(1,2-C2B9H11)- anion", Journal of OrganoMetallic Chemistry, Apr. 2002, pp. 1-8, vol. 649, No. 1.

Zubreichuk, Z. et al, "Synthesis and Some Transformations of Complex Salts of Bis-o-dicarbollyliron (II),-cobalt(II), and -nickel(II)", Russian Journal of General Chemistry, Apr. 2001, pp. 531-534, vol. 71. No. 4.

Erdman, A. et al, "Synthesis of New Complex Derivatives of Bis-o-dicarbollyliron" Vestsi Akademii Navuk BSSR, Seryya Khimichnykh Navuk, 1989, pp. 109-110, No. 4.

Plesek, J. et al, "Potential Uses of Metallocarborane Sandwich Anions for Analysis, Characterization and Isolation of Various Cations and Organic Bases", Collection of Czechoslovak Chemical Communications, 1984, pp. 2776-2789, vol. 49.

De Clercq, E. "New Perspectives for the Treatment of HIV Infections", Collection of Czechoslovak Chemical Communications, 1998, pp. 449-479, vol. 63.

Lebron, F. et al, "Approaches to the Design of Effective HIV-1 Protease Inhibitors", Current Medical Chemistry, Apr. 2000, pp. 455-477, vol. 7, No. 4.

Valliant, J. et al, "The Medicinal Chemistry of Carboranes", Coordination Chemistry Reviews, Oct. 2002, pp. 173-230, vol. 232, No. 1-2.

Sivaev, I. et al, "Derivatives of the Closo-Dodecaborate Anion and their Application in Medicine", Russian Chemical Bulletin, Aug. 2002, pp. 1362-5285, vol. 51, No. 8.

* cited by examiner

CHEMICAL COMPOSITION WITH BORANE CLUSTERS FOR USE AS AN HIV PROTEASE INHIBITOR

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to novel HIV protease inhibitors and their use, both in vitro and in vivo.

BACKGROUND OF THE INVENTION

Human immunodeficiency virus (HIV) was identified as etiological agent of AIDS independently in Paris and in Washington (Barre-Sinoussi, F., Chermann, J. C., Rey, F., Nugeyre, M. T., Chamaret, S., Gruest, J., Dauguet, C., Axler-Blin, C., Vezinet-Brun, F., Rouzinoux C., Rozenbaum W., Montagnier, L. (1983) Science 220, 868-871; Popovic, M., Sarngadharan, M. G., Read, E., Gallo, R. C. (1984) Science 224, 497-500). In last 18 years, the efforts towards the development of active virostatics lead to the inventions of many medicaments, that strongly contributed to the treatment of this disease. Despite that, the scientists still did not succeed in controlling and stopping the spread of the disease. AIDS is still a serious worldwide problem. Especially in developing countries and in central Africa the epidemy has catastrophical extent endangering the basic social and national principles.

Human immunodeficiency virus (HIV) belongs to the genus Lentivirus, family Retroviridae. Viruses belonging to this family contain diploid RNA genome and use reverse transcriptase for their replication. Retroviruses are further divided into three genera: oncoviruses, lentiviruses and spumaviruses (Gelderblom, H. R., P. A. Marx, M. Ozel, D. Gheysen, R. J. Munn, K. I. Joy, and G. Pauli (1990) Morphogenesis and Fine Structure of Lentiviruses. In Pearl, Lawrence (Ed.). Retroviral Proteinases: Control of Maturation and Morphogenesis). The genus Lentivirus involves viruses causing slow chronical diseases. The most important representatives are HIV-1, HIV-2 (both further referred to under common abbreviation HIV) and the simian lentivirus SIV.

Mature virion HIV is a spherical particle with the diameter of 100 to 110 nm. The nucleus of the virus, encapsulated by capsid protein, consists of two copies of the genomic single-stranded RNA, nucleocapsidic proteins (NC) and viral enzymes reverse transcriptase (RT), integrase (IN) and protease (PR). The external capsid consists of phospholipid membrane derived from the host cell. Button-shaped structures, consisting of three molecules of glycosylated surface protein SU loosely embedded into transmembrane protein TM, extrude from the capsid (Gelderblom, H. R., P. A. Marx, M. Ozel, D. Gheysen, R. J. Munn, K. I. Joy, and G. Pauli (1990) Morphogenesis and Fine Structure of Lentiviruses. In Pearl, Lawrence (Ed.). Retroviral Proteinases: Control of Maturation and Morphogenesis).

HIV genome is formed by two identical RNA molecules of the size of about 9.2 kb, encoding for 9 various genes. The basic structure of the genome, characteristic for all the retroviruses, consists of three structural genes gag, pol and env. In addition to structural genes, 6 genes encoding for proteins with regulatory functions, participating in the virus' replication, were identified in the HIV genome.

Replication cycle of the HIV inside the host cell can be divided into several stages (Carrasco L., Sonenberg N., Wimmwe E. (1993) Regulation of Gene Expression in Animal Viruses, ed. by L. Carrasco, et al., Plenum Press, New York): surface glycoprotein of the viral capsid SU recognizes and binds with high affinity the protein receptor CD4+, which is expressed on the surface of T-lymphocytes. For effective binding a coreceptor, specific according to the host cell type, is necessary. Virus enters the cell by endocytosis or by fusion of the virus capsid with the cell surface and the content of the capsid gets into the cell cytoplasm. The reverse transcriptase (RT) transcripts the viral RNA into the double-stranded DNA, that is integrated into the host cell chromosome by the enzyme integrase (IN). So the virus persists in the idle state (latent infection) until the moment of activation and transcription of viral genes by the host RNA polymerase II. According to the proviral mRNA, viral polyprotein precursors Gag and Gag-Pol are synthesized at the ribosomes. Posttranslationally modified polyproteins and genomic RNA are collected close to the cell surface and during the process called budding the virions are released from the cell. In the immature particle, the polyprotein precursors Gag and Gag-Pol are cleaved by virus-encoded protease (PR), yielding functional proteins, creating thereby the mature infectious particle. If the HIV PR is afflicted or its activity is inhibited, the virion remains immature.

Most extensively examined is HIV-1 PR. It is a dimeric aspartate protease, consisting of two identical non-covalently bonded subunits. The primary structure of the monomeric subunit consists of 99 amino acids. The most important contribution to the knowledge of the HIV-1 PR secondary structure were the crystallographic structural analyses (Wlodawer, A., Miller, M., Jaskólski, M., Sathyanarayana, B. K., Baldwin, E., Weber, I. T., Selk, L. M., Clawson, L., Schneider, J., Kent, S. B. (1989) Science 245, 616-621), that disclosed the double rotational $C_2$ symmetry and high content of β-structures. Four of the chains in the core of the molecule form a leaf of the shape of the "letter Ψ", that is characteristic for all the aspartate proteases. Triplet of the active site (Asp25-Thr26-Gly27) is placed in the bend of the protein chain and its structure is stabilized by hydrogen bonds net.

HIV PR must first be autocatalytically cleaved out of the polyprotein precursor and subsequently it cleaves the precursor in nine exactly defined sites. HIV PR specifically cleaves the viral polyprotein despite the fact, that the amino acid sequences of the sites cleaved rather differ. In contrast to other endopeptidases (pepsin, trypsin, renin), that hydrolyze peptide bonds next to particular amino acids, in the HIV PR no analogous relation to the primary structure can be defined. Instead, specificity stemming from the cumulative effect of independent mostly weak interactions among individual side chains of the substrate and the corresponding subsite of the enzyme is assumed. Important is the effect of hydrophobic interaction, surface, polarity, potential of the secondary structure etc. (Poorman, R. A., Tomasselli, A. G., Heinrikson, R. L., Kézdy, F. J. (1991) J. Biol. Chem. 266, 14554-14561).

HIV Protease Inhibitors

Several steps of the HIV life cycle were chosen as the targets of therapeutical treatment. The most important are the reverse transcriptase (dideoxynucleosides, their analogs and non-nucleoside inhibitors), binding and entry of the virion into the host cell (soluble CD4 receptors and their derivatives, polyanionic compounds, fusion inhibitors), integration of the provirus by the integrase into the host chromosome, regulation of the transcription by protein products of the genes tat and rev etc. (review: De Clercq, E. (1998) *Collect. Czech. Chem. Commun.* 63, 449-479). Maturation of the retrovirus and above all its most important enzyme HIV protease, that is the object of this patent application, is also the object of extensive research and the rational designing of medicaments. In the Czech Republic seven inhibitors were or are going to be approved for clinical use: saquinavir, ritonavir, indinavir, nelfinavir, amprenavir, lopinavir and atazanavir. All these inhibitors competitively inhibit binding of the natural substrates to HIV PR and decrease the infectivity of the virus by blocking the virion maturation.

Development of the Resistance Against the HIV PR Inhibitors

Launching the protease inhibitors in the years 1995-1996 and introduction of HAART—highly active antiretroviral therapy lead to moderation of onset of opportunic infections and decrease in mortality. This had increased the hope of patients and physicians for developing sufficient therapy of AIDS. Unfortunately, soon after the launch of the new medicaments also their limits were found.

When PR inhibitor is applied, it suppresses the virus replication. If the replication is not fully suppressed, a small population of the virus, which is resistant to the inhibitor, can survive under the selection pressure. This leads to the resistance of the virus (Larder, B., Richman, D., Vella, S. (1998) *HIV resistance and implications for therapy*, MediCom Inc., Atlanta, USA). Until now, the mutations in at least 49 positions in 99-amino acid monomer were observed (Gulnik, S., Erickson, J. W., Xie, D. (2000) *Vitam. Horm.* 58, 213-256).

The essential factors responsible for quick development of resistant varieties are natural variability of HIV genome (polymorphism) and dynamic virus replication during the latent phase and during the idle state (Erickson, J. W., Burt, S. K. (1996) *Annu. Rev. Pharmacol. Toxicol.* 36, 545-571). The genetical variability of HIV probably stems from the combination of high error rate of reverse transcriptase, genome recombination and selection pressure of human immunity system.

There are several possible strategies, that virus can use in order to develop its resistance against protease inhibitors. Among the most important are: mutations in the binding site of the enzyme, which directly influence binding; mutations outside the binding site of the enzyme, which indirectly influence binding; mutations of the cleaved sites of the HIV PR in polyprotein substrates. Also mutations that decrease the stability of the HIV PR dimer and thereby its affinity to the inhibitor can contribute to the resistance, and finally also mutations outside the protease area that can result for example in more effective shift of the reading frame (Erickson, J. W., Burt, S. K. (1996) *Annu. Rev. Pharmacol. Toxicol.* 36, 545-571; Boden, D., Markowitz, M. (1998) *Antimicrob. Agents Chemother.* 42, 2775-2783).

The HIV protease inhibitors known so far can be divided into three basic groups: (i) compounds designed as isosters of the substrate transition state (statine, hydroxyethylaminic, hydroxymethylenic, hydroxyethylenic type, α,α'-difluoroketones, etc.) (ii) compounds proposed with the aid of rational design on the basis of geometric similarity to the substrate (e.g. DMP inhibitors) (iii) compounds having accidental structural similarity to the substrate, obtained by the screening of natural substances isolated e.g. from biological material (Lebon F., Ledecq M. (2000) *Curr. Med. Chem.* 7, 455-477).

Design of viral protease inhibitors is a non-trivial problem. In contrast to many other enzymes, whose substrate is a simple organic molecule (e.g. the natural substrate of nitrogen (II) oxide synthase is L-arginin, so simple modifications like $N^\omega$—OH—Arg či $N^\omega$-Me-Arg are succesful inhibitors), the design of HIV protease inhibitors is much more complicated issue. Its natural substrate is polypeptide, that is recognized in a specific site and cleaved, yielding functional enzymes and structural proteins of the virion. Theoretically, both by methods of molecular modelling and by ab initio calculations, and also practically the design of specific HIV protease inhibitor represents difficult problem, when low-molecular substrate must show higher affinity to the enzyme than natural polypeptide does.

All HIV protease inhibitors used in the treatment (saquinavir, ritonavir, indinavir, nelfinavir, amprenavir, lopinavir and atazanavir) can be classified into group (i). They have peptidomimetic character and are competitive inhibitors of the active site of the enzyme. Such compounds usually show unfavourable pharmacodynamic properties (in order to reach the effective concentration level in infected cells it is necessary to administer orally rather high doses of the medicaments) and later the resistance can develop. In order to overcome the resistance problem there is considerable effort devoted to discovering non-peptide inhibitors, that could be developed by rational design on the basis of structural information, obtained by rentgenostructural analysis of complexes of HIV PR and known inhibitors, eventually by screening of combinatorial or other libraries of chemical compounds.

BRIEF SUMMARY OF THE INVENTION

The above mentioned disadvantages are eliminated by HIV protease inhibitors of this invention, which contain clusters selected from the group consisting of boranes and/or carboranes and/or metallacarboranes having 6 to 12 boron atoms in each cluster, wherein the charge of each individual borane, carborane or metallacarborane cluster is 0, −1 or −2; the number of borane, carborane or metallacarborane clusters in the inhibitor molecule is 1 to 9, and the carborane clusters in metallacarborane inhibitors are coordinated to transition metal atom, selected from the group containing cobalt, iron, nickel and ruthenium.

Another compounds of this invention are the HIV protease inhibitors containing the above mentioned clusters, wherein heteroatoms, selected from the group containing nitrogen, phosphorus, silicon, germanium, tin and sulphur, can be present in the clusters.

The first aspect of the invention are HIV protease inhibitors of the general formula $$(R^1)_n A(\text{—X—Y—Z})_m \qquad (I),$$

wherein A is anionic cluster $B_{10}H_{10}^{(2-)}$, $B_{12}H_{12}^{(2-)}$, $CB_6H^{7(-)}$, $CB_7H_8^{(-)}$, $CB_9H_{10}^{(-)}$, $CB_{10}H_{11}^{(-)}$, $CB_{11}H_{12}^{(-)}$, $SiB_{11}H_{12}^{(-)}$, $SiB_{11}H_{11}^{(2-)}$, $SnB_{11}H_{11}^{(2-)}$, $GeB_{11}H_{11}^{(2-)}$, $7,8\text{-}C_2B_9H_{12}^{(-)}$, $7,9\text{-}C_2B_9H_{12}^{(-)}$, $Si_2B_{10}H_{12}^{(-)}$, $[(1,2\text{-}C_2B_9H_{11})_2\text{-}3\text{-Co(III)}]^{(-)}$, $[(1,7\text{-}C_2B_9H_{11})_2\text{-}3\text{-Co(III)}]^{(-)}$, $[(C_2B_9H_{11})\text{Co(III)}(C_2B_8H_{10})_2\text{Co(III)}(C_2B_9H_{11})]^{(2-)}$, $[(1,2\text{-}C_2B_9H_{11})_2\text{-}3\text{-Fe(III)}]^{(-)}$, $[(1,7\text{-}C_2B_9H_{11})_2\text{-}3\text{-Fe(III)}]^{(-)}$, $[(1,2\text{-}C_2B_9H_{11})_2\text{-}3\text{-Ni(III)}]^{(-)}$, $[1\text{-}(C_5H_5)\text{Fe(III)}(CB_{10}H_{11})]^{(-)}$, $[(C_5H_5)\text{Co(III)}(1,2\text{-}CB_{10}H_{11})]^{(-)}$, $[(C_5H_5)\text{Ni(III)}(1,2\text{-}CB_{10}H_{11})]^{(-)}$, $[(C_2B_{10}H_{12})_2 M(\text{III})]^{(-)}$ or neutral cluster $1,2\text{-}C_2B_8H_{10}$, $1,6\text{-}C_2B_8H_{10}$, 1,10-$C_2B_8H_{10}$, 1,2-$C_2B_{10}H_{12}$, 1,7-$C_2B_{10}H_{12}$, 1,12-$C_2B_{10}H_{12}$, $P_2B_{10}H_{10}$, $SB_{11}H_{11}$, $NB_{11}H_{11}$, $PB_{11}H_{11}$, [[($C_5H_5$)(1,2-$C_2B_9H_{11}$)-3-Co(III)], [($C_5H_5$)(1,7-$C_2B_9H_{11}$)-2-Co(III)], [($C_5H_5$)(1,2-$C_2B_9H_{11}$)-3-Fe(III)], [($C_5H_5$)(1,7-$C_2B_9H_{11}$)-2-Fe(III)], [($C_5H_5$)(1,2-$C_2B_9H_{11}$)Ni(III)], [($C_5H_5$)Fe(II)($C_3B_8H_{11}$)], [($C_5H_5$)Ru(II)($C_3B_8H_{11}$)], [($C_3B_8H_{11}$)$_2$-Fe(II)], [($C_5H_5$)Fe(II)($C_3B_7H_{10}$)], [1-($C_5H_5$)Fe(II)($PC_2B_8H_{10}$)], [($C_2B_9H_{11}$)-Co(III)($C_3B_8H_{11}$)], [($C_2B_{10}H_{12}$)-M(III)($C_5H_5$)]

wherein substituents of the general formula —X—Y—Z and $R^1$ are bound to carbon atoms, boron atoms or heteroatoms of cluster A, wherein j is 1 to 3, M represents Fe, Co, Ni, Ru, and wherein $R^1$ is the same or different and is selected from the group containing hydrogen, halogen, methyl, hydroxy, phenyl, phenylene, thiol, methoxy and trifluoromethoxy group, m is 0, 1 or 2, n is 0 to 12, X is the same or different and represents —O—, —C(=O)—, —$CH_2$—, —N($R^3$)—, —P($R^3$)—, —S—, $C_1$ to $C_{10}$ alkanediyl, —($CH_2CH_2O$)$_q$—, —O($CH_2CH_2O$)$_q$—, —(O$CH_2CH_2$)$_q$—, —($CH_2CH_2O$)$_q$$CH_2CH_2$—, —(O$CH_2CH_2$)$_q$N($R^3$)—, —(O$CH_2CH_2$)$_q$$N^+$($R^3$)($R^7$)—, —(O$CH_2CH_2$)$_q$N($R^3$)($CH_2CH_2O$)$_q$—, —(O$CH_2CH_2$)$_q$$N^+$($R^3$)($R^7$)($CH_2CH_2O$)$_q$—, phenylene substituted independently with 0 to 3 $R^{14}$, in case of metallacarboranes of the type [(1,2-$C_2B_9H_{11}$)$_2$-3-M(III)]$^{(-)}$ X represents one of the bridging groups >S, >N, >N($R^3$)$^+$, >P, >$O_2$P, >$O_2$P(=O), phenylene substituted independently with 0 to 3 $R^{14}$, ethandiyl substituted independently with 0 to 3 $R^{14}$, substituent Y is connected to this bridging group, wherein M is as defined above, wherein q is 0 to 12, wherein $R^3$ is the same of different and represents hydrogen, A, —($CH_2CH_2O$)$_q$—A, —S(=O)$_k$($R^7$), —C(=O)($R^5$), —S(=O)$_2$N($R^7$)($R^8$), $C_1$-$C_8$ alkyl substituted with 0 to 3 $R^{10}$, $C_2$-$C_8$ alkenyl substituted with 0 to 3 $R^{10}$, $C_2$-$C_8$ alkynyl substituted with 0 to 3 $R^{10}$, phenyl substituted with 0 to 5 $R^{10}$, naphtyl substituted with 0 to 5 $R^{10}$, adamanthyl substituted with 0 to 5 $R^{10}$, and $C_3$-$C_{14}$ carbocyclic residue substituted with 0 to 5 $R^{10}$ or 0 to 5 $R^{11}$, or 5- to 10-membered heterocycle containing 1 to 4 heteroatoms selected from the group containing oxygen, sulphur and nitrogen or the same heterocycle substituted with 0 to 4 $R^{11}$, wherein q is as defined above, wherein k is 0, 1 or 2, wherein $R^{10}$ is the same or different and represents hydrogen, keto group, halogen, cyano group, —$CH_2$N($R^7$)($R^8$), —N($R^7$)($R^8$), —C(=O)O($R^7$), —C(=O)($R^5$), —OC(=O)($R^7$), —O($R^7$), $C_2$-$C_6$ alkoxyalkyl, —S(=O)$_k$($R^7$), —NHC(=NH)NH($R^7$), —C(=NH)NH($R^7$), —C(=O)N($R^7$)($R^8$), —N($R^8$)C(=O)($R^7$), =N—O($R^8$), —N($R^8$)C(=O)O($R^8$), —OC(=O)N($R^7$)($R^8$), —N($R^7$)C(=O)N($R^7$)($R^8$), —N($R^8$)S(=O)$_2$N($R^7$)($R^8$), —N($R^8$)S(=O)$_2$($R^7$), —S(=O)$_2$N($R^7$)($R^8$), $C_1$-$C_4$ alkyl, $C_2$-$C_4$ alkenyl, $C_3$-$C_{10}$ cycloalkyl, $C_3$-$C_6$ cycloalkylmethyl, phenyl, pentafluorophenyl, phenylmethyl, phenethyl, phenoxy, phenylmethoxy, nitro, $C_7$-$C_{10}$ arylalkyl, —C(=O)—NH(OH), —C(=O)—NH($NH_2$), —B(OH)$_2$, sulfonamide, formyl, $C_3$-$C_6$ cycloalkoxy, $C_1$-$C_4$ alkyl substituted with —N($R^7$)($R^8$), $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —O$CH_2$C(=O)O($R^7$), 2-(1-morpholino)ethoxy, azido, —C($R^8$)=N—O($R^8$), $C_5$-$C_{14}$ carbocyclic residue substituted with 0 to 5 $R^{11}$, or 5- to 10-membered heterocycle containing 1 to 4 heteroatoms selected independently from the group containing oxygen, sulphur and nitrogen or the same heterocycle substituted with 0 až 2 $R^{11}$, wherein k is as defined above, wherein $R^7$ is the same or different and represents hydrogen, phenyl substituted with 0 to 3 $R^{14}$, phenylmethyl substituted with 0 to 3 $R^{14}$, $C_1$-$C_6$ alkyl substituted with 0 to 3 $R^{14}$, $C_2$-$C_4$ alkenyl substituted with 0 to 3 $R^{14}$, $C_1$-$C_6$ alkylcarbonyl substituted with 0 to 3 $R^{14}$, $C_1$-$C_6$ alkoxycarbonyl substituted with 0 to 3 $R^{14}$, $C_1$-$C_6$ alkylaminocarbonyl substituted with 0 to 3 $R^{14}$, $C_3$-$C_6$ alkoxyalkyl substituted with 0 to 3 $R^{14}$, any group commonly used for protecting amino group, if $R^7$ is bound to nitrogen atom, or any group commonly used for protecting hydroxy group, if $R^7$ is bound to oxygen atom, wherein $R^{14}$ is the same or different and represents hydrogen, keto, halogen, cyano group, —$CH_2NH_2$, —$NH_2$, —C(=O)OH, —OC(=O)($C_1$-$C_3$ alkyl), —OH, $C_2$-$C_6$ alkoxyalkyl, —C(=O)$NH_2$, —OC(=O)$NH_2$, —NHC(=O)$NH_2$, —S(=O)$_2NH_2$, $C_1$-$C_4$ alkyl, $C_2$-$C_4$ alkenyl, $C_3$-$C_{10}$ cycloalkyl, $C_3$-$C_6$ cycloalkylmethyl, phenyl, benzyl, phenethyl, phenoxy, benzyloxy, nitro, $C_1$-$C_{10}$ arylalkyl, —C(=O)—NH(OH), —C(=O)—NH($NH_2$), —B(OH)$_2$, $C_3$-$C_6$ cycloalkoxy, $C_1$-$C_4$ alkyl substituted with —$NH_2$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —O$CH_2$C(=O)OH, 2-(1-morpholino)ethoxy, azido, aryl($C_1$-$C_3$ alkyl), $C_5$-$C_{14}$ carbocyclic residue, 5- to 10-membered heterocycle containing 1 to 4 heteroatoms selected independently from the group containing oxygen, sulphur and nitrogen, or the same heterocycle substituted with 0 to 3 $R^6$, wherein $R^6$, if it is bound to carbon atom, is the same or different and represents phenyl, phenylmethyl, phenethyl, phenoxy, phenylmethoxy, halogen, hydroxy, nitro, cyano group, $C_1$-$C_4$ alkyl, $C_3$-$C_6$ cycloalkyl, $C_3$-$C_6$ cycloalkylmethyl, $C_7$-$C_{10}$ arylalkyl, $C_1$-$C_4$ alkoxy, —C(=O)OH, —C(=O)—NH(OH), —C(=O)—NH($NH_2$), —B(OH)$_2$, sulfonamide, formyl, $C_3$-$C_6$ cycloalkoxy, —O($R^7$), $C_1$-$C_4$ alkyl substituted with —N($R^7$)($R^8$), —N($R^7$)($R^8$), $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —S(=O)$_k$($R^7$), —S(=O)$_2$N($R^7$)($R^8$), —NHS(=O)$_2$($R^8$), —O$CH_2$C(=O)OH, 2-(1-morpholino)ethoxy, —C($R^8$)=N—O($R^8$), 5- to 10-membered heterocycle containing 1 to 4 heteroatoms selected independently from the group containing oxygen, sulphur and nitrogen, or the same heterocycle substituted with 0 to 3 $R^9$, $C_3$-$C_4$ carbon chain that is bound with its other end to the neighboring carbon atom of the ring and so creates 5- or 6-membered ring, this 5- or 6-membered ring can be substituted at any of the aliphatic carbon atoms with halogen group, $C_1$-$C_4$ alkyl, $C_1$-$C_4$ alkoxy, hydroxy, —N($R^7$)($R^8$), or if $R^6$ is bound to saturated carbon atom, $R^6$ can be =O or =S, wherein k and $R^7$ are as defined above, wherein $R^8$ is the same or different and represents hydrogen, hydroxy, trifluoromethyl, $C_1$-$C_6$ alkoxy, $C_2$-$C_6$ alkenyl, phenylmethyl, amino, $C_1$-$C_6$ alkyl, $C_1$-$C_6$ alkyl substituted with 0 to 3 groups selected independently from the group containing hydroxy, $C_1$-$C_4$ alkoxy, halogen, amino, any group commonly used for protecting amino group, if $R^8$ is bound to nitrogen atom, or any group commonly used for protecting hydroxy group, if $R^8$ is bound to oxygen atom, wherein $R^9$ is the same or different and represents hydrogen or methyl, wherein $R^6$, if it is bound to nitrogen atom, is the same or different and represents phenyl, phenylmethyl, phenethyl, hydroxy, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —$CH_2N(R^7)(R^8)$, —$N(R^7)(R^8)$, $C_2$-$C_6$ alkoxyalkyl, $C_1$-$C_4$ haloalkyl, $C_1$-$C_4$ alkoxycarbonyl, —C(=O)OH, $C_1$-$C_4$ alkylcarbonyloxy, $C_1$-$C_4$ alkylcarbonyl $C(R^8)$=N—O($R^8$), wherein $R^7$ and $R^8$ are as defined above, $R^7$ and $R^8$ can alternatively be connected so that they create the groups —$(CH_2)_4$—, —$(CH_2)_5$—, —$CH_2CH_2N(R^9)CH_2CH_2$— or —$CH_2CH_2OCH_2CH_2$—, wherein $R^5$ is the same or different and represents hydrogen, halogen, phenylmethyl, phenethyl, —C(=O)—NH(OH), —C(=O)—NH(NH$_2$), —B(OH)$_2$, sulfonamide, azido, formyl, phenoxy, phenylmethoxy, nitro, cyano group, —$CH_2N(R^7)(R^8)$, —$N(R^7)(R^8)$, —$OCH_2C$(=O)OH, —C(=O)O($R^7$), —OC(=O)($R^7$), —O($R^7$), $C_2$-$C_6$ alkoxyalkyl, —S(=O)$_k$($R^7$), —NHC(=NH)NH($R^7$), —C(=NH)NH($R^7$), —C(=O)N($R^7$)($R^8$), —$N(R^8)C$(=O)($R^7$), =N—O($R^8$), —$N(R^8)C$(=O)O($R^8$), OC(=O)N($R^7$)($R^8$), —$N(R^7)C$(=O)N($R^7$)($R^8$), —$C(R^8)$=N—O($R^8$), —$N(R^8)S$(=O)$_2$N($R^7$)($R^8$), —$N(R^8)S$(=O)$_2$($R^7$), —S(=O)$_2$N($R^7$)($R^8$), $C_1$-$C_4$ alkyl, $C_2$-$C_4$ alkenyl, $C_3$-$C_{10}$ cycloalkyl, $C_3$-$C_6$ cycloalkylmethyl, $C_7$-$C_{10}$ arylalkyl, $C_3$-$C_6$ cycloalkoxy, $C_1$-$C_4$ alkyl substituted with —$N(R^7)(R^8)$, $C_1$-$C_4$ hydroxyalkyl, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, 2-(1-morpholino)ethoxy, —($C_1$-$C_3$ alkyl)aryl substituted with 0 to 2 $R^6$, $C_5$-$C_{14}$ carbocyclic residue substituted with 0 to 3 $R^6$, 5- to 10-member heterocycle containing 1 to 4 heteroatoms selected independently from the group containing oxygen, sulphur and nitrogen, or the same heterocycle substituted with 0 to 3 $R^6$, wherein k, $R^6$, $R^7$ and $R^8$ are as defined above, wherein $R^{11}$, if it is bound to carbon atom, is the same or different and represents phenethyl, phenoxy, $C_3$-$C_{10}$ cycloalkyl, $C_3$-$C_6$ cycloalkylmethyl, $C_7$-$C_{10}$ arylalkyl, —C(=O)—NH(NH$_2$), $C_2$-$C_6$ alkoxyalkyl, methylenedioxy, ethylenedioxy, $C_1$-$C_4$ alkylcarbonyloxy, —NHS(=O)—($R^8$), phenylmethoxy, halogen, 2-(1-morpholino)ethoxy, —C(=O)O($R^7$), —C(=O)—NH(OH), —C(=O)N($R^7$)N($R^7$)($R^8$), cyano group, —B(OH)$_2$, sulfonamide, formyl, $C_3$-$C_6$ cycloalkoxy, $C_1$-$C_4$ haloalkyl, $C_1$-$C_4$ haloalkoxy, $C_2$-$C_4$ haloalkenyl, $C_2$-$C_4$ haloalkynyl, —$N(R^7)(R^8)$, —$C(R^8)$=N—O($R^8$), —NO$_2$, —O($R^7$), —$N(R^{12})(R^{13})$, —S(=O)$_k$($R^7$), —S(=O)$_k$N($R^7$)($R^8$), —C(=O)N($R^7$)($R^8$), —OC(=O)N($R^7$)($R^8$), —C(=O)($R^5$), —OC(=O)($R^5$), —OC(=O)O($R^7$), phenyl, —C(=O)N($R^7$)—($C_1$-$C_4$ alkyl), N($R^7$)($R^8$), —C(=O)N($R^{12}$)($R^{13}$), —C(=O)—($C_1$-$C_4$ alkyl)—N($R^7$)C(=O)O($R^7$), $C_1$-$C_4$ alkoxy substituted with 0 to 4 groups selected independently from the group containing $R^5$, $C_3$-$C_6$ cycloalkyl, —C(=O)O($R^7$), —C(=O)N($R^7$)($R^8$), —$N(R^7)(R^8)$ or hydroxyl, $C_1$-$C_4$ alkyl substituted with 0 to 4 groups selected independently from the group containing $R^5$, =N($R^8$), =NN($R^7$)C(=O)N($R^7$)($R^8$) or —$N(R^7)(R^8)$, $C_2$-$C_4$ alkenyl substituted with 0 to 4 $R^5$, $C_2$-$C_4$ alkynyl substituted with 0 to 4 $R^5$, 5- to 6-membered heterocycle containing 1 to 4 heteroatoms selected independently from the group containing oxygen, sulphur and nitrogen, $C_3$-$C_4$ carbon chain, whose other end is bound to the next carbon atom of the ring, thereby creating 5- or 6-membered ring, this 5- or 6-membered ring can be on any aliphatic carbon atom substituted with halogen, $C_1$-$C_4$ alkyl, $C_1$-$C_4$ alkoxy, hydroxy, —$N(R^7)(R^8)$, or if $R^{11}$ is bound to saturated carbon atom, $R^{11}$ can be =O or =S, wherein k, $R^5$, $R^7$ and $R^8$ are as defined above, wherein $R^{12}$ is the same or different and represents hydrogen or $C_1$-$C_3$ alkyl, wherein $R^{13}$ is the same or different and represents —C(=O)N($R^7$)($R^8$), —C(=O)N($R^7$)NH($R^8$), —C(=O)C($R^5$)$_2$N($R^7$)($R^8$), —C(=O)C($R^5$)$_2$N($R^7$)NH($R^8$), —C(=O)C($R^5$)$_2$N($R^7$)C(=O)O($R^7$), —C(=O)H, —C(=O)($R^5$), —C(=O)—($C_1$-$C_4$ alkyl)—N($R^7$)($R^8$), —C(=O)—($C_1$-$C_4$ alkyl)—, N($R^7$)C(=O)O($R^7$) or 1 to 3 amino acids bound by amide bonds to nitrogen atom via carboxyl groups, wherein $R^5$, $R^7$ and $R^8$ are as defined above, wherein $R^{11}$, if it is bound to nitrogen atom, is the same or different and represents phenyl, phenylmethyl, phenethyl, hydroxyl, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —$CH_2N(R^7)(R^8)$, —$N(R^7)(R^8)$, $C_2$-$C_6$ alkoxyalkyl, $C_1$-$C_4$ haloalkyl, $C_1$-$C_4$ alkoxycarbonyl, —C(=O)OH, $C_1$-$C_4$ alkylcarbonyloxy, $C_1$-$C_4$ alkylcarbonyl or —$C(R^8)$=N—O($R^8$), wherein $R^7$ and $R^8$ are as defined above, wherein $R^{11}$, if it is bound to sulphur atom, represents =O, wherein Y is the same or different and represents $C_1$-$C_{10}$ alkandiyl substituted with 0 to 4 substituents selected independently from the group containing $R^2$ and $R^3$; $C_1$-$C_{10}$ cycloalkandiyl substituted with 0 to 4 $R^2$; —X—; —C(=O)—; —(CH$_2$CH$_2$O)$_q$—; —O(CH$_2$CH$_2$O)$_q$—; —(OCH$_2$CH$_2$)$_q$—; —(CH$_2$CH$_2$O)$_q$CH$_2$CH$_2$—; —S(=O)$_k$—; —P(=O)(OR$^3$)—X—; —P(=O)(N($R^3$)($R^4$))—X—; —P(=O)(N($R^3$)($R^4$))—X—; —C(=O)—X—; —(CF$_2$)$_q$—; phenylen substituted independently with 0 to 3 $R^{14}$, wherein k, q, X, $R^3$ and $R^{14}$ are as defined above, wherein $R^2$ is the same or different and represents hydrogen, —A, —X—A, —O($R^7$), —S($R^7$), —N($R^7$), —C(=O)O($R^7$), keto group, $C_1$-$C_8$ alkyl substituted with 0 to 3 $R^5$, $C_2$-$C_8$ alkenyl substituted with 0 to 3 $R^5$, phenyl, benzyl, phenyl substituted independently with 0 to 5 $R^{14}$, alkynyl substituted with 0 to 3 $R^5$, $C_1$-$C_8$ perfluoroalkyl, $C_3$-$C_{14}$ carbocycle substituted with 0 to 3 $R^5$ or 0 to 3 $R^6$, or 5- to 10-membered heterocycle containing 1 to 4 heteroatoms selected from the group containing oxygen, sulphur and nitrogen, or the same heterocycle substituted with 0 to 2 $R^{11}$, oligoethylene glycol, $R^6$, wherein A, X, $R^5$, $R^6$, $R^7$, $R^{11}$ and $R^{14}$ are as defined above, wherein $R^4$ is the same or different and represents hydrogen, $C_1$-$C_8$ alkyl substituted with 0 to 3 $R^{10}$, $C_2$-$C_8$ alkenyl substituted with 0 to 3 $R^{10}$, $C_2$-$C_8$ alkynyl substituted with 0 to 3 $R^{10}$, a $C_3$-$C_{14}$ carbocyclic residue substituted with 0 to 5 $R^{10}$ or 0 to 5 $R^{11}$, or 5- to 10-membered heterocycle containing 1 to 4 heteroatoms selected from the group containing oxygen, sulphur and nitrogen, or the same heterocycle substituted with 0 to 2 $R^{11}$, wherein $R^{10}$ and $R^{11}$ are as defined above, wherein Z is the same or different and represents hydrogen, A, —X—A, (—X—A)$_2$, —C(=O)—X—A, —CH(OH)—X—A, —CH(NH$_2$)—X—A, —NH—A, —NH—CH(OH)CH—NH—A, —S(=O)$_k$—X—A, —O—P(=O)(OR$^3$)—X—A, —O—P(=O)(N(R$^3$)(R$^4$))—X—A, R$^3$, R$^7$, R$^{10}$, C$_1$-C$_{10}$ alkyl substituted with 0 to 4 R$^2$, —OH, —O(R$^3$), calix[4]arene substituted with 0 to 4 R$^3$, wherein k, A, X, R$^2$, R$^3$, R$^4$, R$^7$ and R$^{10}$, are as defined above and the pharmaceutically acceptable salts thereof.

Another aspect of the invention are HIV protease inhibitors of the general formula (II)

$$(R^1)_n A(-X-Z)_m \quad (II),$$

wherein A, X, Z and R$^1$ and m,n are as defined above and the pharmaceutically acceptable salts thereof.

Yet another aspect of the invention are compounds, that are also HIV protease inhibitors:

Abbr.: Compound:

GB-1 [(8-HO-(CH$_2$-CH$_2$O)$_2$-1,2-C$_2$B$_9$H$_{10}$)(1',2'-C$_2$B$_9$H$_{11}$)-3,3'-Co]Na

GB-8 [8-(OH-1,2-C$_2$B$_9$H$_{10}$)(1',2'-C$_2$B$_9$H$_{11}$)-3,3'-Co]Na.nH$_2$O

GB-12 [8,8'-μ-O-(1,2-C$_2$B$_9$H$_{10}$)(1',2'-C$_2$B$_9$H$_{10}$)-3,3'-Co]Na

GB-16 [8-(O-P(=O)(OH)$_2$)-(1,2-C$_2$B$_9$H$_{10}$)(1',2'-C$_2$B$_9$H$_{11}$)-3,3'-Co]Na.nH$_2$O

GB-19 [(1,2-C$_2$B$_9$H$_{11}$)-3,3'-Co-8',10'-(OH)$_2$-(1,2-C$_2$B$_8$H$_{10}$)-3"Co-(1",2"-C$_2$B$_9$H$_{11}$)]Na$_2$

GB-21 [(8-((C$_6$H$_5$)(OH)CH-CH-O-(CH$_2$-CH$_2$O)$_2$)-1,2-C$_2$B$_9$H$_{10}$)(1',2'-C$_2$B$_9$H$_{11}$)-3,3'-Co]Na

GB-22 [(1,2-C$_2$B$_9$H$_{10}$)-3,3'-Co(1',2'-C$_2$B$_9$H$_{11}$)-8-(OCH$_2$CH$_2$)$_2$O-CH(C$_6$H$_5$)CH(C$_6$H$_5$)(OCH$_2$CH$_2$)$_2$-8"-O-(1",2"-C$_2$B$_9$H$_{10}$)-3",3"'-Co(1"',2"'-C$_2$B$_9$H$_{11}$)]Na$_2$

GB-23 [(C$_2$B$_9$H$_{10}$)$_2$-3-Fe]Na.4H$_2$O

GB-24 [(1,2-C$_2$B$_9$H$_{10}$)-3,3'-Co(1',2'-C$_2$B$_9$H$_{10}$)-8,8'-μ-NH-CH$_2$-CH(OH)-CH$_2$-8"',8"'-μ-NH-(1",2"-C$_2$B$_9$H$_{10}$)-3"',3"'-Co(1"',2"'-C$_2$B$_9$H$_{10}$)]

GB-25 [(1,2-C$_2$B$_9$H$_{10}$)-3,3'-Co(1',2'-C$_2$B$_9$H$_{11}$)-8-(OCH$_2$CH$_2$)$_4$-8"-O-(1",2"-C$_2$B$_9$H$_{10}$)-3",3"'-Co(1"',2"'-C$_2$B$_9$H$_{11}$)]Na$_2$

GB-26 [8,8'-μ-(1,2-C$_6$H$_4$)-(1,2-C$_2$B$_9$H$_{10}$)(1',2'-C$_2$B$_9$H$_{11}$)-3,3'-Co]Na

GB-27 [4,8'-8,4'-μ-(1,2-C$_6$H$_4$)$_2$(1,2-C$_2$B$_9$H$_9$)(1',2'-C$_2$B$_9$H$_9$)-3,3'-Co]Na

GB-28 [8,8'-μ-((4-C$_6$H$_5$)-1,2-C$_6$H$_3$)-(1,2-C$_2$B$_9$H$_{10}$)(1',2'-C$_2$B$_9$H$_{10}$)-3,3'-Co]Na

GB-29 [4,8'-μ-((4-CH$_3$)-1,2-C$_6$H$_4$)-8,4'-μ-((5-CH$_3$)-1,2-C$_6$H$_4$)-(1,2-C$_2$B$_9$H$_9$)(1',2'-C$_2$B$_9$H$_9$)-3,3'-Co]Na

GB-30 [8,8'-μ-((4-CH$_3$)(5-CH$_3$)-1,2-C$_6$H$_4$)-(1,2-C$_2$B$_9$H$_{10}$)(1',2'-C$_2$B$_9$H$_{10}$)-3,3'-Co]Na

GB-31 [(1,2-C$_2$B$_9$H$_{11}$)-3,3'-Co-(1,2-C$_2$B$_8$H$_{10}$)-3"Co-(1",2"-C$_2$B$_9$H$_{11}$)]Na$_2$

GB-35 [(1,2-C$_2$B$_9$H$_{10}$)-3,3'-Co(1',2'-C$_2$B$_9$H$_{11}$)-8-(OCH$_2$CH$_2$)$_2$O-$_{D,L}$-CH(C$_6$H$_5$)CH(C$_6$H$_5$)CH(C$_6$H$_5$)(OCH$_2$CH$_2$)$_2$-8"-O-(1",2"-C$_2$B$_9$H$_{10}$)-3",3"'-Co(1"',2"'-C$_2$B$_9$H$_{11}$)]Na$_2$

GB-40 [(8-(C$_6$H$_5$)-(CH$_2$-CH$_2$O)$_2$)-1,2-C$_2$B$_9$H$_{10}$)(1',2'-C$_2$B$_9$H$_{11}$)-3,3'-Co]Na

GB-41 [(8-((3-CF$_3$)-C$_6$H$_4$O-(CH$_2$-CH$_2$O)$_2$)-1,2-C$_2$B$_9$H$_{10}$)(1',2'-C$_2$B$_9$H$_{11}$)-3,3'-Co]Na

GB-42 [(8-((2-CH$_2$-C$_6$H$_5$)-C$_6$H$_4$O-(CH$_2$-CH$_2$O)$_2$)-1,2-C$_2$B$_9$H$_{10}$)(1',2'-C$_2$B$_9$H$_{11}$)-3,3'-Co]Na

GB-43 [(8-((4-C(C$_6$H$_5$)$_3$)-C$_6$H$_4$O-(CH$_2$-CH$_2$O)$_2$)-1,2-C$_2$B$_9$H$_{10}$)(1',2'-C$_2$B$_9$H$_{11}$)-3,3'-Co]Na

GB-44 [(8-((4-C$_6$H$_5$)-C$_6$H$_4$O-(CH$_2$-CH$_2$O)$_2$)-1,2-C$_2$B$_9$H$_{10}$)(1',2'-C$_2$B$_9$H$_{11}$)-3,3'-Co]Na

GB-45 [(8-(C$_6$F$_5$O-(CH$_2$-CH$_2$O)$_2$)-1,2-C$_2$B$_9$H$_{10}$)(1',2'-C$_2$B$_9$H$_{11}$)-3,3'-Co]Na

GB-46 [(1,2-C$_2$B$_9$H$_{10}$)-3,3'-Co(1',2'-C$_2$B$_9$H$_{11}$)-8-(OCH$_2$CH$_2$)$_2$NH(CB$_{10}$H$_{10}$)-CH$_2$CH$_2$OCH$_2$CH$_2$-8"-O-(1",2"-C$_2$B$_9$H$_{10}$)-3",3"'-Co(1"',2"'-C$_2$B$_9$H$_{11}$)]Na$_2$

GB-47 [(8-((2-OCH$_3$)-C$_6$H$_4$O-(CH$_2$-CH$_2$O)$_2$)-1,2-C$_2$B$_9$H$_{10}$)(1',2'-C$_2$B$_9$H$_{11}$)-3,3'-Co]Na

GB-48 [(1,2-C$_2$B$_9$H$_{10}$)-3,3'-Co(1',2'-C$_2$B$_9$H$_{11}$)-8-(OCH$_2$CH$_2$)$_2$NH(CH$_2$CH$_2$CH$_2$CH$_3$)-CH$_2$CH$_2$OCH$_2$CH$_2$-8"-O-(1",2"-C$_2$B$_9$H$_{10}$)-3",3"'-Co(1"',2"'-C$_2$B$_9$H$_{11}$)]Na

GB-49 [(8-((CB$_{10}$H$_{10}$)NH-(CH$_2$-CH$_2$O)$_2$)-1,2-C$_2$B$_9$H$_{10}$)(1',2'-C$_2$B$_9$H$_{11}$)-3,3'-Co]K

GB-50 [(1,2-C$_2$B$_9$H$_{10}$)-3,3'-Co(1',2'-C$_2$B$_9$H$_{11}$)-8-(OCH$_2$CH$_2$)$_2$N(CH$_2$CH$_3$)$_2$-CH$_2$CH$_2$OCH$_2$CH$_2$-8"-O-(1",2"-C$_2$B$_9$H$_{10}$)-3",3"'-Co(1"',2"'-C$_2$B$_9$H$_{11}$)]Na

GB-51 [(8-((4-CH$_3$)-C$_6$H$_4$-SO$_2$NH-(CH$_2$-CH$_2$O)$_2$)-1,2-C$_2$B$_9$H$_{10}$)(1',2'-C$_2$B$_9$H$_{11}$)-3,3'-Co]Na

GB-52 [(8-((4-CH$_3$)-C$_6$H$_4$-SO$_2$N(CH$_2$CH$_2$CH$_2$CH$_3$)-(CH$_2$-CH$_2$O)$_2$)-1,2-C$_2$B$_9$H$_{10}$)(1',2'-C$_2$B$_9$H$_{11}$)-3,3'-Co]Na

GB-53 [(8-(((CH$_2$)$_6$(CH)$_3$CCH$_2$-O-(CH$_2$-CH$_2$O)$_2$)-1,2-C$_2$B$_9$H$_{10}$)(1',2'-C$_2$B$_9$H$_{11}$)-3,3'-Co]Na

GB-54 [(8-(C$_6$F$_5$O-(CH$_2$)$_5$O)-1,2-C$_2$B$_9$H$_{10}$)(1',2'-C$_2$B$_9$H$_{11}$)-3,3'-Co]Na

GB-55 [(8-((C$_6$H$_5$CH$_2$OCH$_2$)$_2$(HOCH$_2$)C-CH$_2$O-(CH$_2$-CH$_2$O)$_2$)-1,2-C$_2$B$_9$H$_{10}$)(1',2'-C$_2$B$_9$H$_{11}$)-3,3'-Co]Na

GB-56 [(1,2-C$_2$B$_9$H$_{10}$)-3,3'-Co(1',2'-C$_2$B$_9$H$_{11}$)-8-(OCH$_2$CH$_2$)$_2$OCH$_2$C(C$_6$H$_5$CH$_2$OCH$_2$)CH$_2$(OCH$_2$CH$_2$)$_2$-8"-O-(1",2"-C$_2$B$_9$H$_{10}$)-3",3"'-Co(1"',2"'-C$_2$B$_9$H$_{11}$)]Na$_2$

GB-57 [(1,2-C$_2$B$_9$H$_{10}$)-3,3'-Co(1',2'-C$_2$B$_9$H$_{11}$)-8-(OCH$_2$CH$_2$)$_2$N(SO$_2$((4-CH$_3$)-C$_6$H$_5$))-CH$_2$CH$_2$OCH$_2$CH$_2$-8"-O-(1",2"-C$_2$B$_9$H$_{10}$)-3",3"'-Co(1"',2"'-C$_2$B$_9$H$_{11}$)]Na$_2$

GB-58 [(8-((C$_6$H$_5$CH$_2$)$_2$CH-O-(CH$_2$-CH$_2$O)$_2$)-1,2-C$_2$B$_9$H$_{10}$)(1',2'-C$_2$B$_9$H$_{11}$)-3,3'-Co]Na

GB-59 [(8-((C$_6$H$_5$CH$_2$)$_2$CH-(CH$_2$)$_5$O)-1,2-C$_2$B$_9$H$_{10}$)(1',2'-C$_2$B$_9$H$_{11}$)-3,3'-Co]K

GB-60 [(8-((5-(CH$_3$)$_2$N)-1-C$_{10}$H$_6$-SO$_2$NH-(CH$_2$-CH$_2$O)$_2$)-1,2-C$_2$B$_9$H$_{10}$)(1',2'-C$_2$B$_9$H$_{11}$)-3,3'-Co]Na

GB-61 [(8-((C$_2$B$_{10}$H$_{11}$)-O-(CH$_2$-CH$_2$O)$_2$)-1,2-C$_2$B$_9$H$_{10}$)(1',2'-C$_2$B$_9$H$_{11}$)-3,3'-Co]Na

GB-63 [(8-(C$_6$H$_4$(CO)(SO$_2$)N-(CH$_2$-CH$_2$O)$_2$)-1,2-C$_2$B$_9$H$_{10}$)(1',2'-C$_2$B$_9$H$_{11}$)-3,3'-Co]Na

GB-64 [(8-(C$_6$H$_4$(CO)(CO)N-(CH$_2$-CH$_2$O)$_2$)-1,2-C$_2$B$_9$H$_{10}$)(1',2'-C$_2$B$_9$H$_{11}$)-3,3'-Co]Na

GB-65 [(8-(((4-CH$_3$)-C$_6$H$_4$SO$_2$)$_2$N-(CH$_2$-CH$_2$O)$_2$)-1,2-C$_2$B$_9$H$_{10}$)(1',2'-C$_2$B$_9$H$_{11}$)-3,3'-Co]Na

GB-67 [(8-((4-NH$_2$)-C$_6$H$_4$-SO$_2$NH-(CH$_2$-CH$_2$O)$_2$)-1,2-C$_2$B$_9$H$_{10}$)(1',2'-C$_2$B$_9$H$_{11}$)-3,3'-Co]Na

GB-69 [(8-(NH$_3$-(CH$_2$-CH$_2$O)$_2$)-1,2-C$_2$B$_9$H$_{10}$)(1',2'-C$_2$B$_9$H$_{11}$)-3,3'-Co]

GB-70 [(1,2-C$_2$B$_9$H$_{10}$)-3,3'-Co(1',2'-C$_2$B$_9$H$_{10}$)-8,8'-μ-NH-CH$_2$CH$_2$OCH$_2$CH$_2$-8"-O-(1",2"-C$_2$B$_9$H$_{10}$)-3",3"'-Co(1"',2"'-C$_2$B$_9$H$_{11}$)]Na

GB-71 [(1,2-C$_2$B$_9$H$_{10}$)-3,3'-Co(1',2'-C$_2$B$_9$H$_{10}$)-8,8'-μ-N(CH$_2$CH$_2$OCH$_2$CH$_2$-8"-O-(1",2"-C$_2$B$_9$H$_{10}$)-3",3"'-Co(1"',2"'-C$_2$B$_9$H$_{11}$))$_2$]Na$_2$

GB-72 [(8-(calix[4]arene-O-(CH$_2$-CH$_2$O)$_2$)-1,2-C$_2$B$_9$H$_{10}$)(1',2'-C$_2$B$_9$H$_{11}$)-3,3'-Co]Na GB-73 [1,3-((1,2-C$_2$B$_9$H$_{10}$)-3,3'-Co(1',2'-C$_2$B$_9$H$_{11}$)-8-(OCH$_2$CH$_2$)$_2$O)$_2$-calix[4]arene]Na$_2$ GB-74 [1,2,3-((1,2-C$_2$B$_9$H$_{10}$)-3,3'-Co(1',2'-C$_2$B$_9$H$_{11}$)-8-(OCH$_2$CH$_2$)$_2$O)$_3$-calix[4]arene]Na$_3$ GB-75 [1,2,3,4-((1,2-C$_2$B$_9$H$_{10}$)-3,3'-Co(1',2'-C$_2$B$_9$H$_{11}$)-8-(OCH$_2$CH$_2$)$_2$O)$_4$-calix[4]arene]Na$_4$ GB-76 [(8-((3-OH)(5-OH)-C$_6$H$_3$O-(CH$_2$-CH$_2$O)$_2$)-1,2-C$_2$B$_9$H$_{10}$)(1',2'-C$_2$B$_9$H$_{11}$)-3,3'-Co]Na GB-77 [(1,2-$C_2B_9H_{10}$)-3,3'-Co(1',2'-$C_2B_9H_{11}$)-8-(OCH$_2$CH$_2$)$_2$(-3-O-($C_6H_3$(1-OH))-5-O)-CH$_2$CH$_2$OCH$_2$CH$_2$-8"-O-(1",2"-$C_2B_9H_{10}$)-3"',3"'-Co(1"',2"'-$C_2B_9H_{11}$)]Na$_2$ GB-78 [1,3,5-((1,2-$C_2B_9H_{10}$)-3,3'-Co(1',2'-$C_2B_9H_{11}$)-8-(OCH$_2$CH$_2$)$_2$O)$_3$-"$C_6H_3$]Na$_3$ GB-79 [((1,2-$C_2B_9H_{10}$)-3,3'-Co(1',2'-$C_2B_9H_{11}$)-8-(OCH$_2$CH$_2$)$_2$O)$_3$-NH]Na$_2$ GB-80 [(1,2-$C_2B_9H_{10}$)-3,3'-Co(1',2'-$C_2B_9H_{11}$)-8-(OCH$_2$CH$_2$)$_2$NH-CH$_2$CH$_2$OCH$_2$CH$_2$-8"-O-(1",2"-$C_2B_9H_{10}$)-3"',3"'-Co(1"',2"'-$C_2B_9H_{11}$)]Na GB-82 [(1,2-$C_2B_9H_{10}$)-3,3'-Co(1',2'-$C_2B_9H_{10}$)-8,8'-μ-S-CH$_2$CH$_2$OCH$_2$CH$_2$-8"-O-(1",2"-$C_2B_9H_{10}$)-3"',3"'-Co(1"',2"'-$C_2B_9H_{11}$)]Na GB-85 [(8-((2-CH$_3$)-$C_6H_4$O-(CH$_2$-CH$_2$O)$_2$)-1,2-$C_2B_9H_{10}$)(1',2'-$C_2B_9H_{11}$)-3,3'-Co]Na GB-87 [(8-(2,6-(CH$_2$C$_6H_5$)$_2$-$C_6H_3$O-(CH$_2$-CH$_2$O)$_2$)-1,2-$C_2B_9H_{10}$)(1',2'-$C_2B_9H_{11}$)-3,3'-Co]Na GB-88 [(8-(2,4,6-(CH$_3$)$_3$-$C_6H_2$O-(CH$_2$-CH$_2$O)$_2$)-1,2-$C_2B_9H_{10}$)(1',2'-$C_2B_9H_{11}$)-3,3'-Co]Na GB-89 [(8-((2-$C_6H_5$)-$C_6H_4$O-(CH$_2$-CH$_2$O)$_2$)-1,2-$C_2B_9H_{10}$)(1',2'-$C_2B_9H_{11}$)-3,3'-Co]Na GB-90 [(8-((2-CH$_3$)-$C_6H_4$-SO$_2$NH-(CH$_2$-CH$_2$O)$_2$)-1,2-$C_2B_9H_{10}$)(1',2'-$C_2B_9H_{11}$)-3,3'-Co]Na GB-91 [(8-(2,4,6-(CH$_3$)$_3$-$C_6H_2$-SO$_2$NH-(CH$_2$-CH$_2$O)$_2$)-1,2-$C_2B_9H_{10}$)(1',2'-$C_2B_9H_{11}$)-3,3'-Co]Na GB-92 [(8-((2-CH$_2$CH$_2$-$C_6H_5$)-$C_6H_4$O-(CH$_2$-CH$_2$O)$_2$)-1,2-$C_2B_9H_{10}$)(1',2'-$C_2B_9H_{11}$)-3,3'-Co]K GB-94 [(8-((2-Br)-$C_6H_4$O-(CH$_2$-CH$_2$O)$_2$)-1,2-$C_2B_9H_{10}$)(1',2'-$C_2B_9H_{11}$)-3,3'-Co]K GB-95 [(8-(2,4,6-(Br)$_3$-$C_6H_2$O-(CH$_2$-CH$_2$O)$_2$)-1,2-$C_2B_9H_{10}$)(1',2'-$C_2B_9H_{11}$)-3,3'-Co]K GB-96 [(8-Cl-1,2-$C_2B_9H_{10}$)(8'-Cl-1',2'-$C_2B_9H_{10}$)-3,3'-Co]Na GB-97 [(8-I-1,2-$C_2B_9H_{10}$)(8'-I-1',2'-$C_2B_9H_{10}$)-3,3'-Co]Na GB-98 [(8,9,12-(Cl)$_3$-1,2-$C_2B_9H_8$)(8',9',12'-(Cl)$_3$-1',2'-$C_2B_9H_8$)-3,3'-Co]K GB-99 [(8,9,12-(Br)$_3$-1,2-$C_2B_9H_8$)(8',9',12'-(Br)$_3$-1',2'-$C_2B_9H_8$)-3,3'-Co]K GB-102 [(8-(NH$_2$(CH$_2$CH$_2$CH$_2$CH$_3$)-(CH$_2$-CH$_2$O)$_2$)-1,2-$C_2B_9H_{10}$)(1',2'-$C_2B_9H_{11}$)-3,3'-Co]

GB-103 [(8-(NH$_2$($C_6H_5$CH$_2$)-(CH$_2$-CH$_2$O)$_2$)-1,2-$C_2B_9H_{10}$)(1',2'-$C_2B_9H_{11}$)-3,3'-Co]

GB-104 [(1,2-$C_2B_9H_{10}$)-3,3'-Co(1',2'-$C_2B_9H_{11}$)-8-(OCH$_2$CH$_2$)$_2$NH(CH$_2$C$_6H_5$)-CH$_2$CH$_2$OCH$_2$CH$_2$-8"-O-(1",2"-$C_2B_9H_{10}$)-3"',3"'-Co(1"',2"'-$C_2B_9H_{11}$)]Na

GB-105 [(1,2-$C_2B_9H_{10}$)-3,3'-Co(1',2'-$C_2B_9H_{11}$)-8-(OCH$_2$CH$_2$)$_2$NH(CH$_2$CH$_2$OH)-CH$_2$CH$_2$OCH$_2$CH$_2$-8"-O-(1",2"-$C_2B_9H_{10}$)-3"',3"'-Co(1"',2"'-$C_2B_9H_{11}$)]Na

GB-106 [(1,2-$C_2B_9H_{10}$)-3,3'-Co(1',2'-$C_2B_9H_{11}$)-8-(OCH$_2$CH$_2$)$_2$NH(C(CH$_3$)$_3$)-CH$_2$CH$_2$OCH$_2$CH$_2$-8"-O-(1",2"-$C_2B_9H_{10}$)-3"',3"'-Co(1"',2"'-$C_2B_9H_{11}$)]Na and the pharmaceutically acceptable salts thereof.

Their structural formulae are depicted on FIG. 1.

Process for preparation of novel compounds GB-21, GB-40, GB-41, GB-43, GB-44, GB-45, GB-49, GB-51, GB-52, GB-53, GB-54, GB-55, GB-58 GB-59, GB-60, GB-61, GB-63, GB-64, GB-65, GB-67, GB-70, GB-76, GB-82, GB-85, GB-87, GB-88, GB-89, GB-90, GB-91, GB-92, GB-94, GB-95, according to the invention comprises the step in which 8-dioxane-cobalt bis(dicarbollide) is treated with compound L—Y—Z, or optionally L—Z, wherein L is selected from the group containing deprotonated hydroxy group and/or amino group and/or substituted amino group and/or amide and/or sulfonamide and/or thioether, and wherein Y and Z are as defined above.

This process was described in literature for another compounds (Plešek J., Grüner B., Heřmánek S., Báča J., Mareček M., Jánchenová J., Lhotský A., Holub K., Selucký P., Rais J., Císařová I., Čáslayský J., *Polyhedron* 2002, 21, 975-86; Grüner B., Plešek J., Báča J., Císařová I., Dozol J-F., Rouquette H., Viñas C., Selucký P., Rais J., *New J.Chem.* 2002, 26, 1519-1527; Sivaev I. B., Starikova Z. A., Sjöberg S., Bregadze V. I., *J. Organomet. Chem.* 2002, 649, 1-8), however here is used in improved fashion for preparation of novel compounds.

Process for preparation of novel compounds GB-22, GB-25, GB-35, GB-46, GB-48, GB-50, GB-56, GB-57, GB-71, GB-77, GB-78, GB-79, GB-80, GB-104, GB-105 and GB-106 according to the invention comprises the step in similar fashion. 8-dioxane-cobalt bis(dicarbollide) is again treated with compound L—Y—Z or L—Z. However, the reaction is performed repeatedly so that more reactive protons are substituted consecutively in polyols, amines, amides and sulfonamides. In this way prepared compounds contain more than one cobalt bis(dicarbollide) clusters. It is advantageous to purify intermediates using liquid chromatography on silica gel.

Process for preparation of novel compounds GB-54 and GB-59 according to the invention comprises the step in which 8-tetrahydrofuran-cobalt bis(dicarbollide) is treated with deprotonated pentafluorophenol or deprotonated dibenzylmethanol.

Process for preparation of novel compound GB-19 according to the invention comprises the step in which compound GB-31 (Canastide) is treated with sulphuric acid solution at elevated temperature. The product is purified by crystallization and liquid chromatography on silica gel.

Process for preparation of novel compound GB-24 according to the invention comprises the step in which compound [(1,2-$C_2B_9H_{10}$)-3,3'-Co(1',2'-$C_2B_9H_{10}$)-8,8'-μ-NH] deprotonated by sodium hydride and dissolved in diethyleneglycol dimethylether (DME) is treated at ambient temperature by epichlorohydrin and the product is obtained by purification of reaction mixture on silica gel column.

Another aspect of the invention is a pharmaceutical composition intended for use in treatment of patients infected by HIV and use in treatment of AIDS containing at least one HIV protease inhibitor selected from the above mentioned compounds of the general formula (I), $(R^1)_nA(—X—Y—Z)_m$ and/or of the general formula (II), $(R^1)_nA(—X—Z)_m$, preferably the above mentioned novel compounds.

Introduction of cluster boron compounds derivatives as new structural element brings very remarkable inhibition properties for HIV protease and its mutants that are resistant against other inhibitors. They are useful both in vitro and in vivo. They are characterized by high effectivity and stability.

DETAILED DESCRIPTION OF THE INVENTION

Examples

This invention is further illustrated by the following examples, which should not be construed as further limiting.
1. Molecular modelling
2. Syntheses of novel compounds
3. Syntheses of known compounds
4. Testing of potency of known and novel compounds in vitro
5. Testing of HIV virus infectivity inhibition in tissue cultures Structures and abbreviations of all compounds taught in the examples are given in FIG. 1. Grey balls represent boron atoms bearing hydrogen or substituent, black balls represent carbon atoms bearing hydrogen or substituent, cobalt and iron atoms are labelled with their symbols. Atoms in clusters are numbered in standard way. The chemical shifts in NMR spectra are given in ppm.

1. Molecular Modelling

The basic philosophic concept of the invention are HIV protease inhibitors containing borane, carborane or metallacarborane clusters. These clusters, in medicine so far designed and used only for neutron capture boron therapy (NCBT) (Larson B. et al. (1997) Advances in Boron Neutron Capture Therapy. Vol. 1, Elsevier Science B.V.; Soloway A. H. et al. (1998) *Chem. Rev.* 98, 1515-1562; Hawthorne M. F., Maderna A. (1999) *Chem. Rev.* 99, 3421-3434; Hawthorne M. F. (1993) *Angew. Chem. Int. Ed.*, 32, 950-984; Valliant J. F. et al. (2002) *Coord. Chem. Rev.* 232, 173-230; Sivaev I. B. et al. (2002) *Russ. Chem. Bull., Int. Ed.*, 51, 1362-1374; Hawthorne M. F., Lee M. W. (2003) *J. Neurooncol.*, 62, 33-45)) represent novel, potentially important structural unit for selective interactions with proteins and thereby development of highly effective and stable non-toxic inhibitors with high therapeutic potential.

For the analysis of the proposed binding mode of inhibitors based on carborane cages to HIV protease by the molecular modelling two compounds were selected: GB-16 and GB-24. Similar compound, $[8,8'-\mu-propargylthio-(1,2-C_2B_9H_{10})_2-3-Co]^-$, was used as starting crystal structure (Cambridge structure database code: TENQAE) (Vohlidal et al. (1996) *Collect. Czech. Chem. Commun.*, 61, 877-887). By molecular modelling method hydrogen atoms were added and sulphur atom was replaced by phosphate group, resp. connecting chain. Atoms or groups added were optimized by semiempirical method MNDO. Compound models were inserted into the active site of the wild type HIV-1 protease according to QF34 inhibitor template (Protein Data Bank code 1IZI). (Weber J., Mesters J. R., Lepsik M., Prejdova J., Svec M., Sponarova J., Mlcochova P., Skalicka K., Strisovsky K., Uhlikova T., Soucek M., Machala L., Stankova M., Vondrasek J., Klimkait T., Kraeusslich H. G., Hilgenfeld R., Konvalinka J. (2002) *J. Mol. Biol.*, 324(4), 739-754).

Figure 1A:
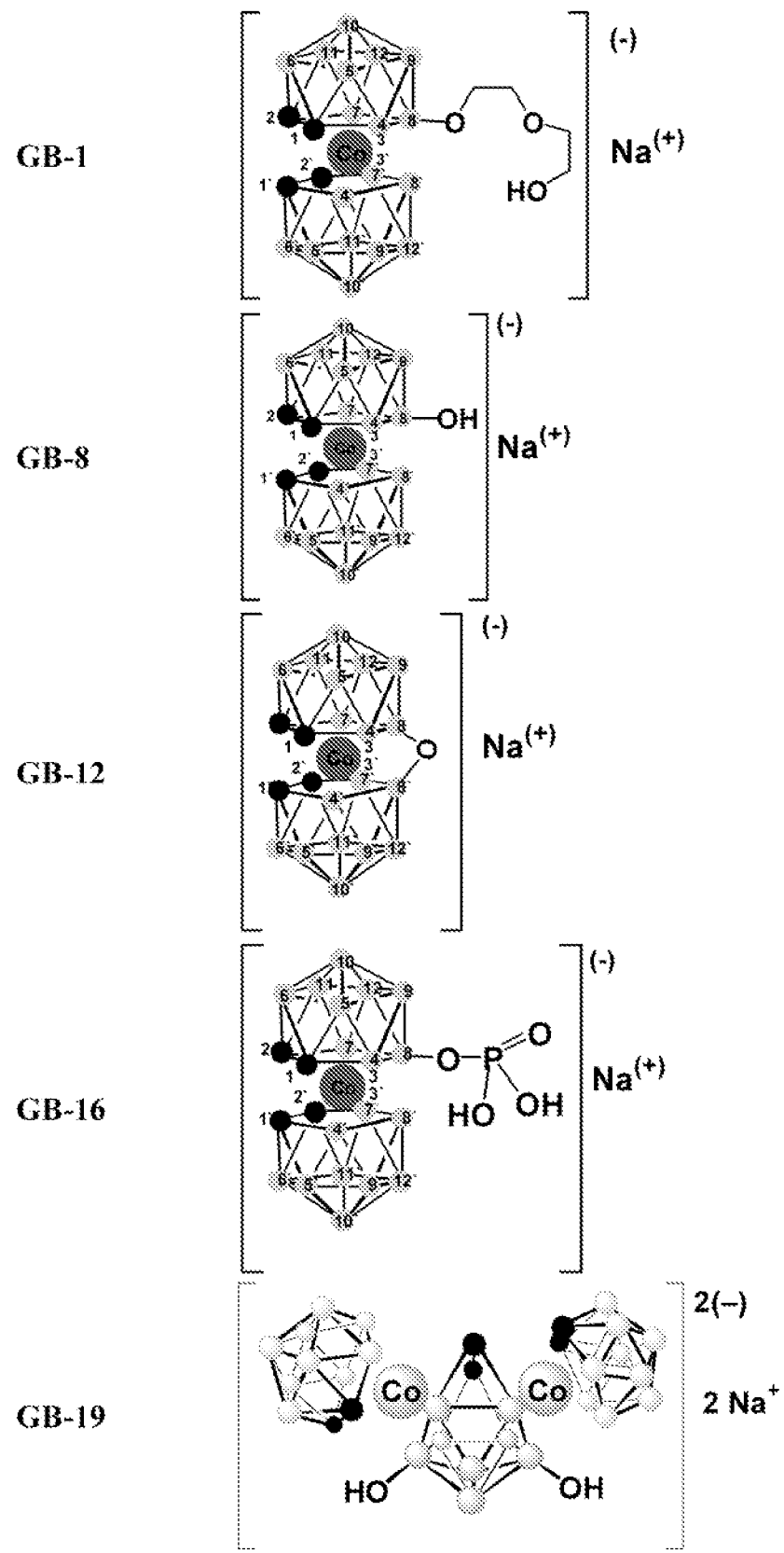
FIG. 1 that is depicted on sheets number 1 to 16 represents structures of the compounds described in the examples. Each compound is labelled by abbreviation.
Figure 1B:
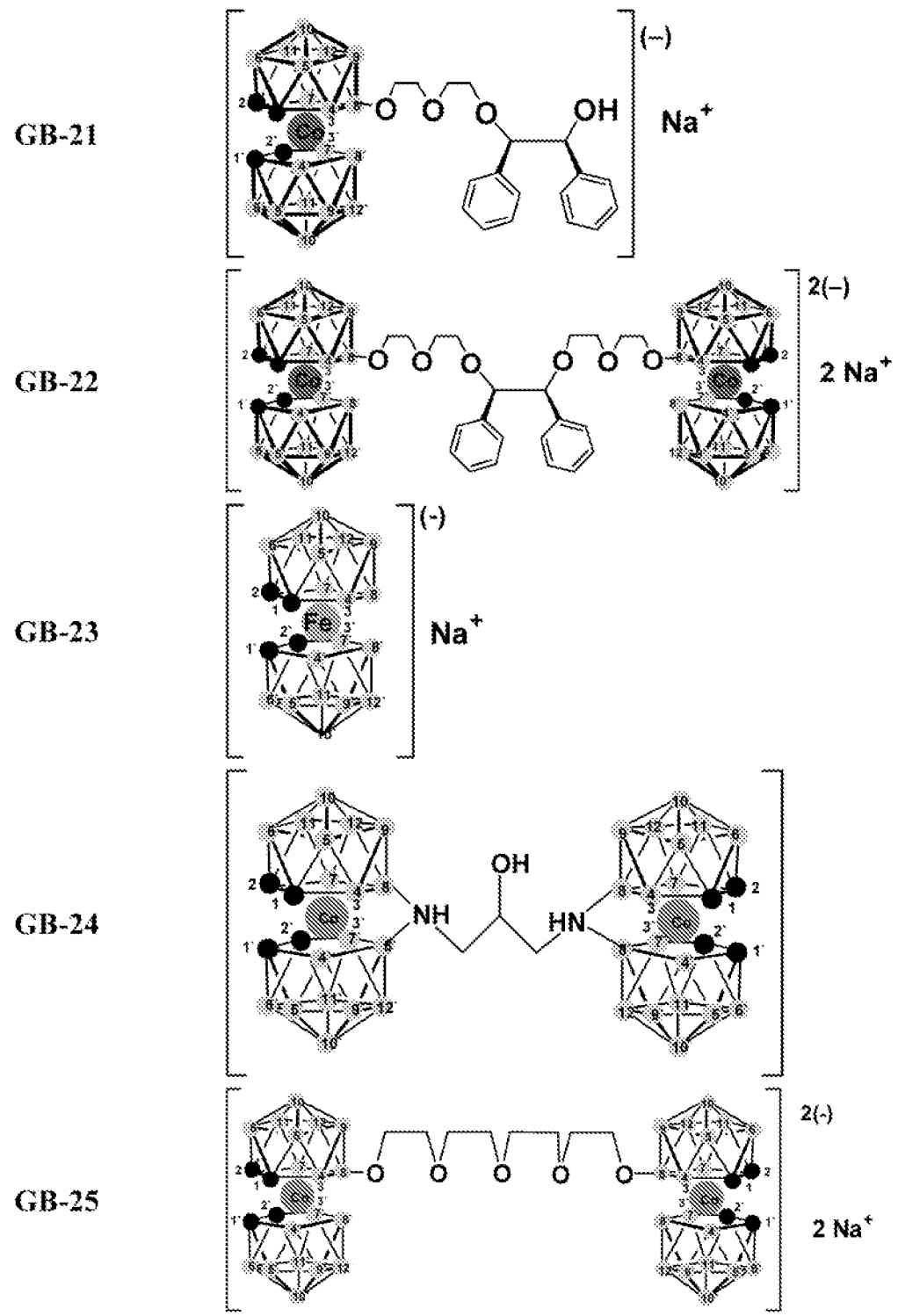
Figure 1C:
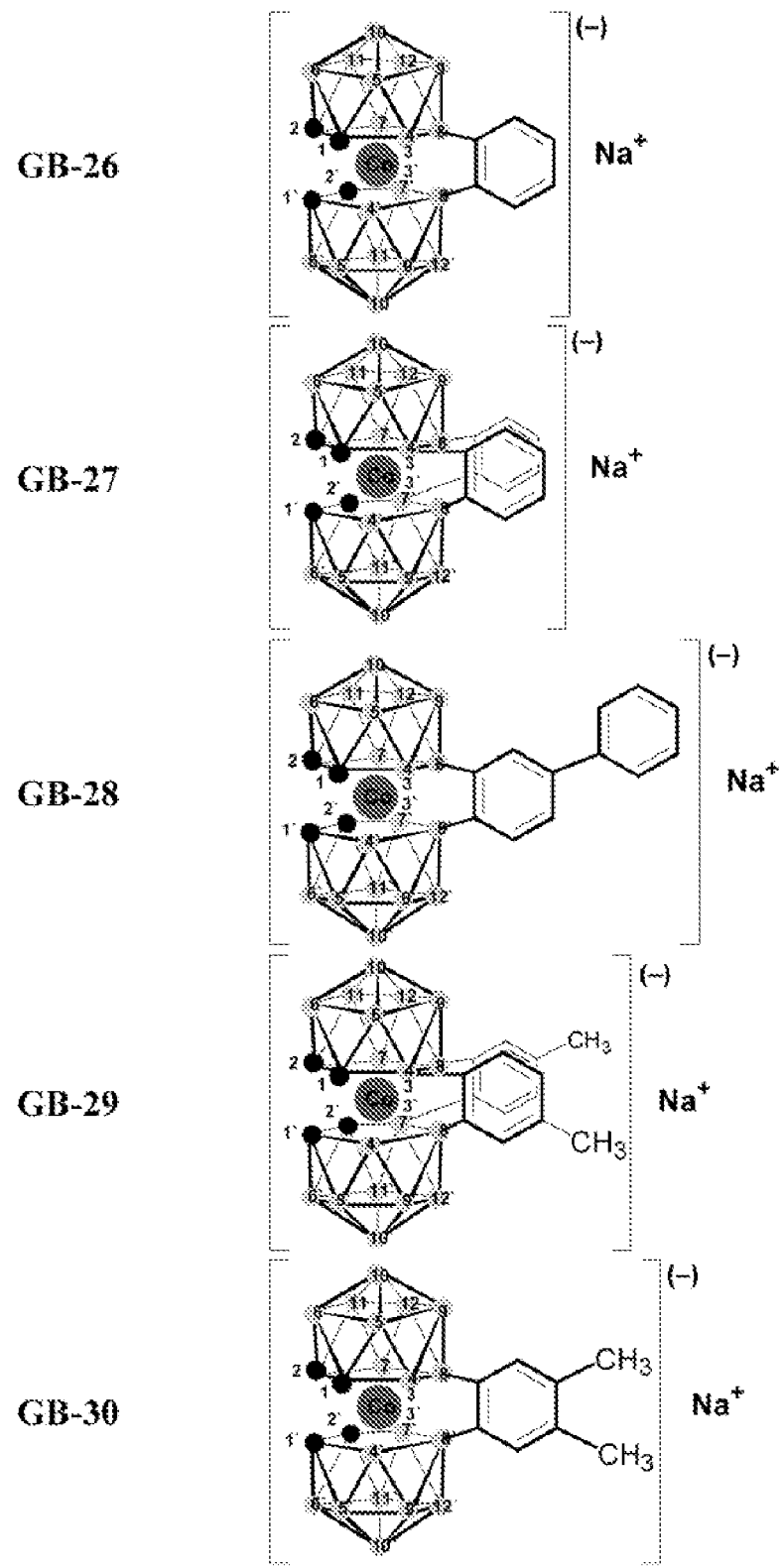
Figure 1D:
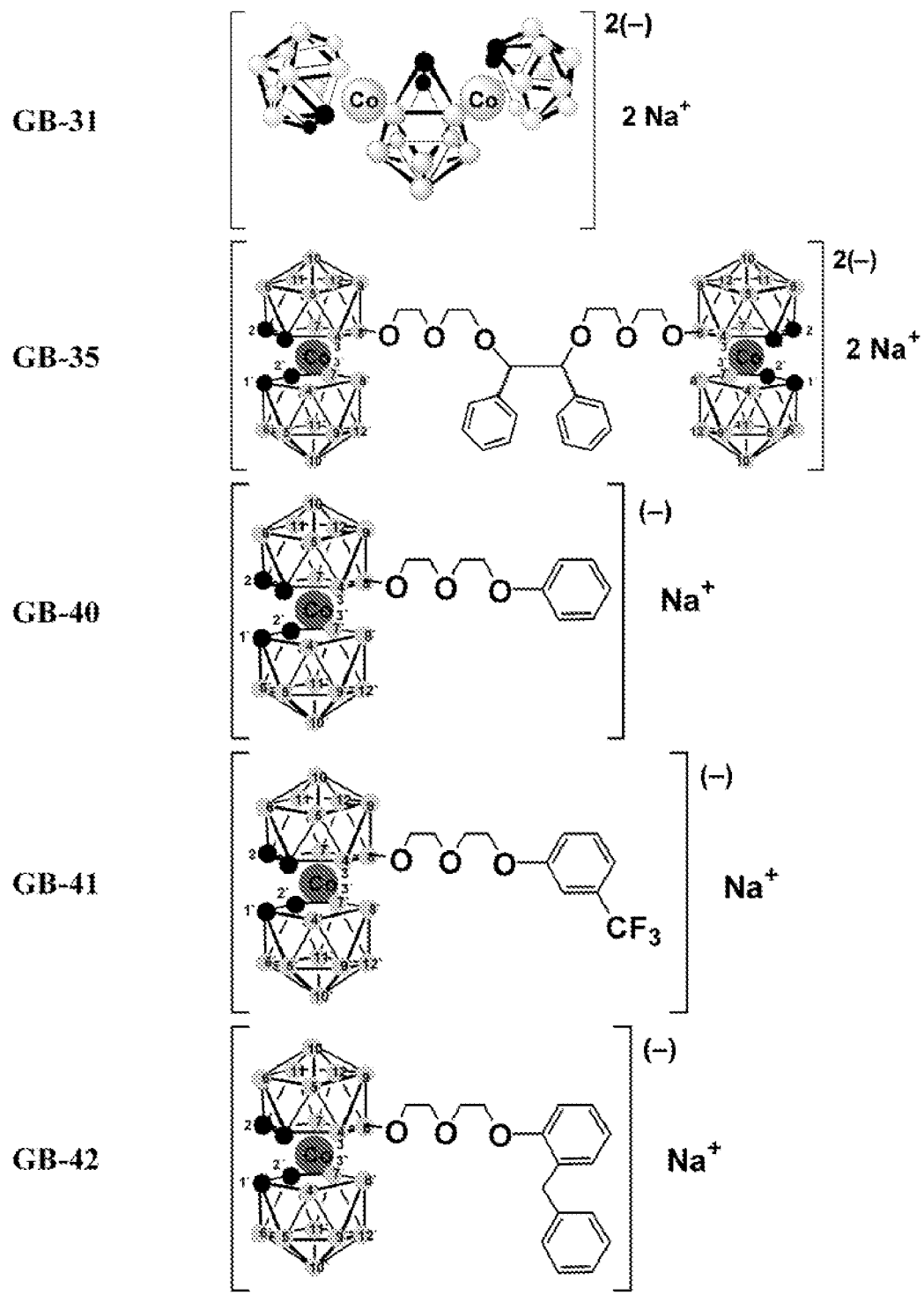
Figure 1E:
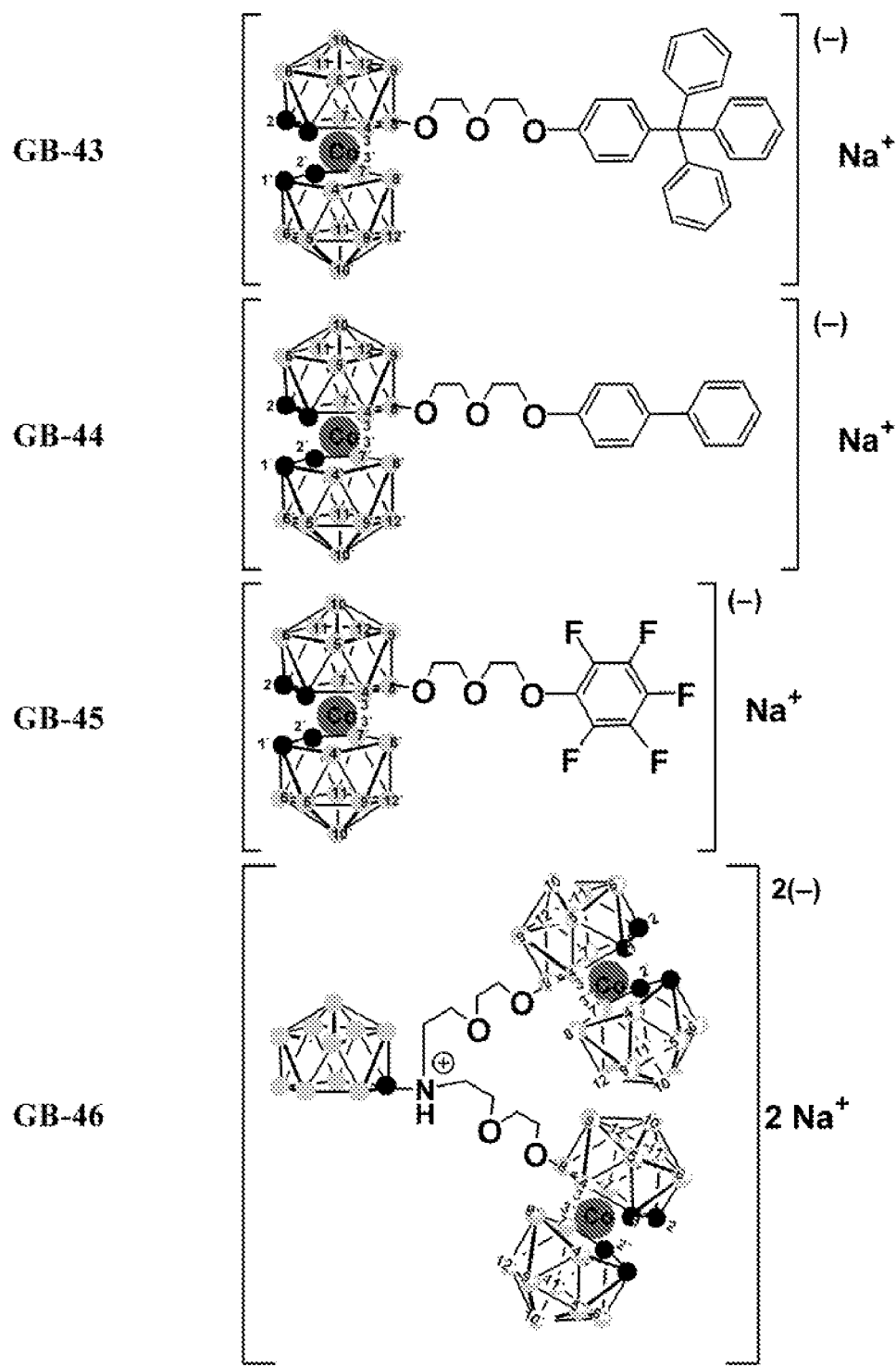
Figure 1F:
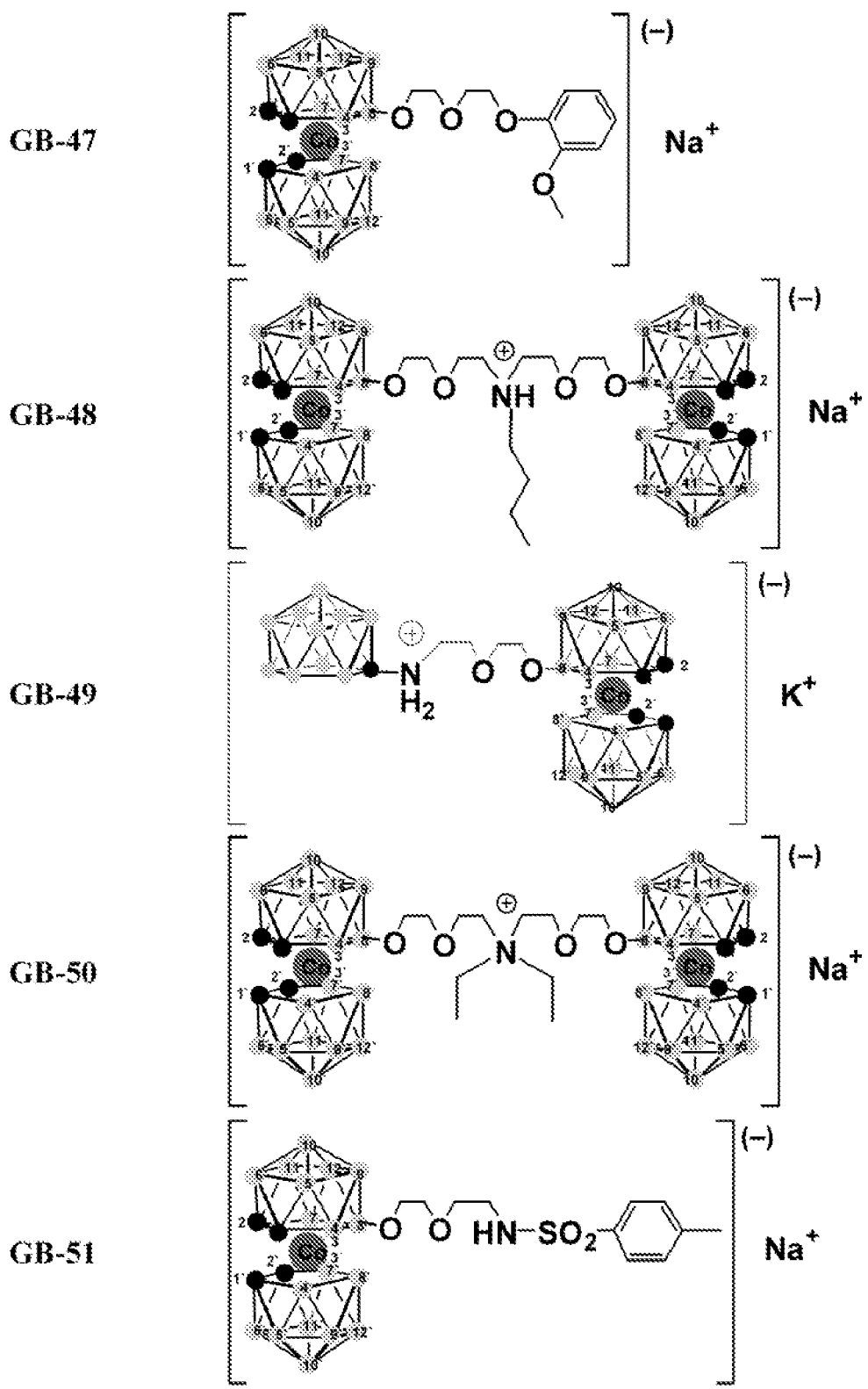
Figure 1G:
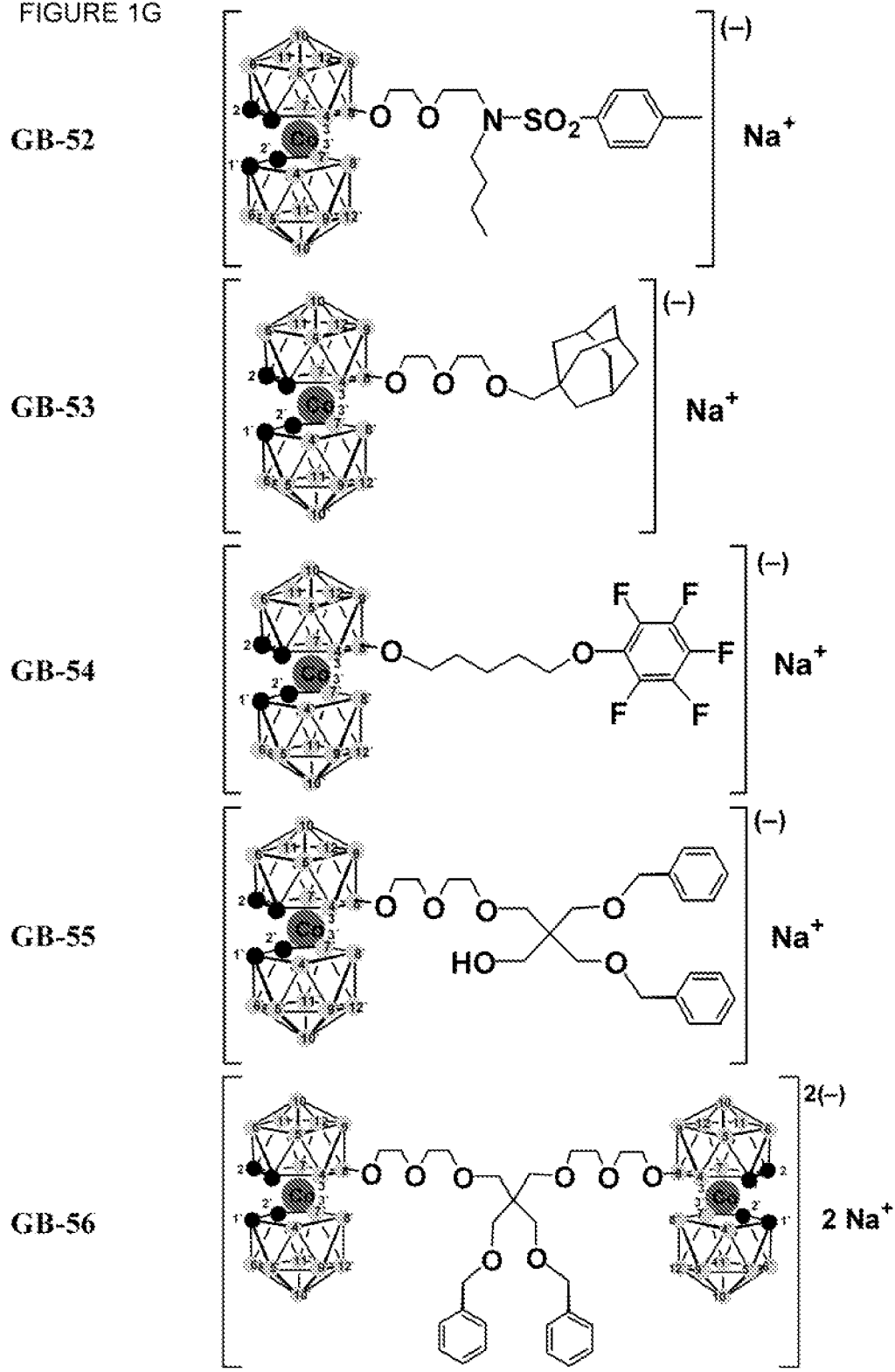
Figure 1H:
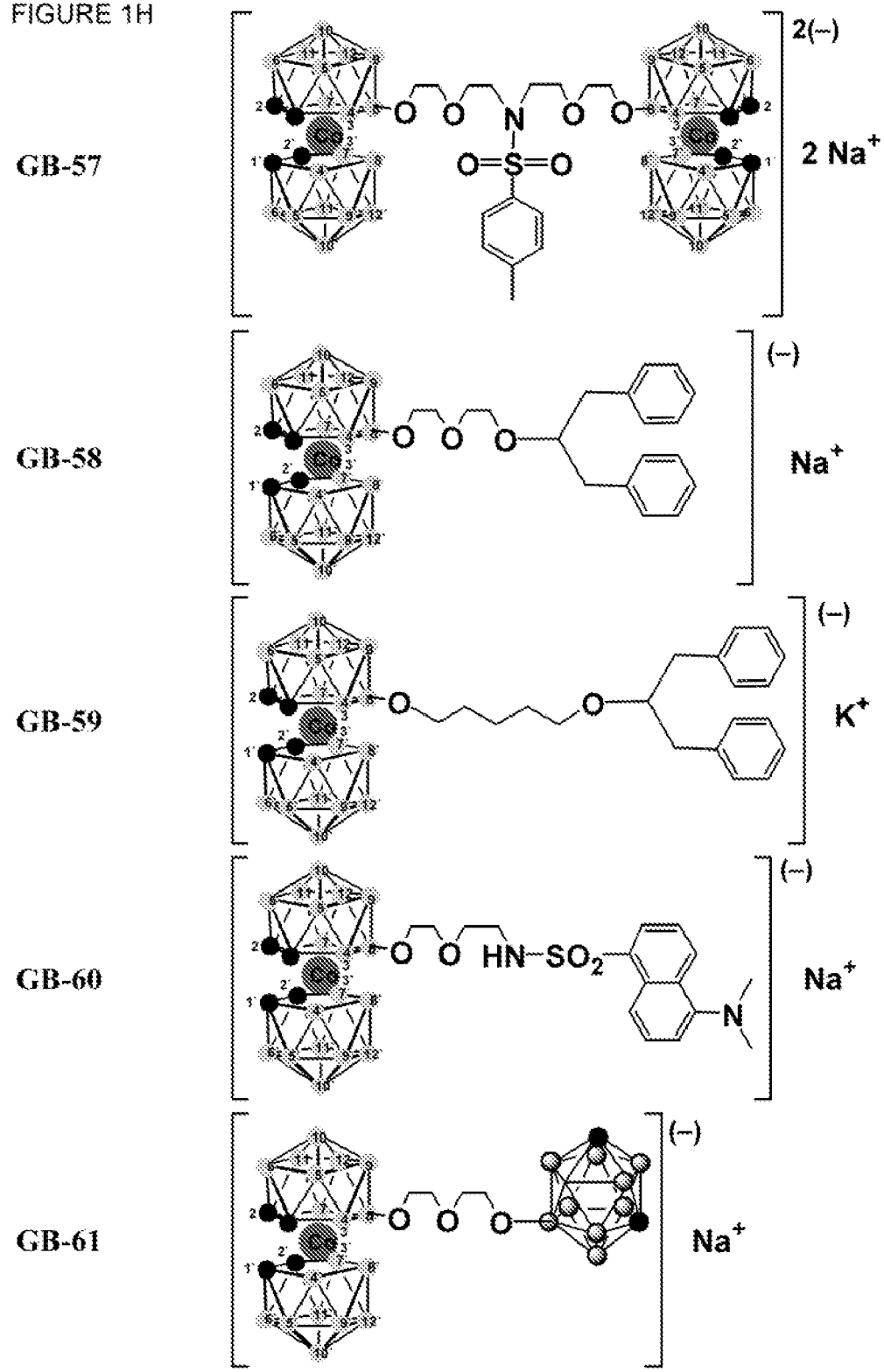
Figure 1I:
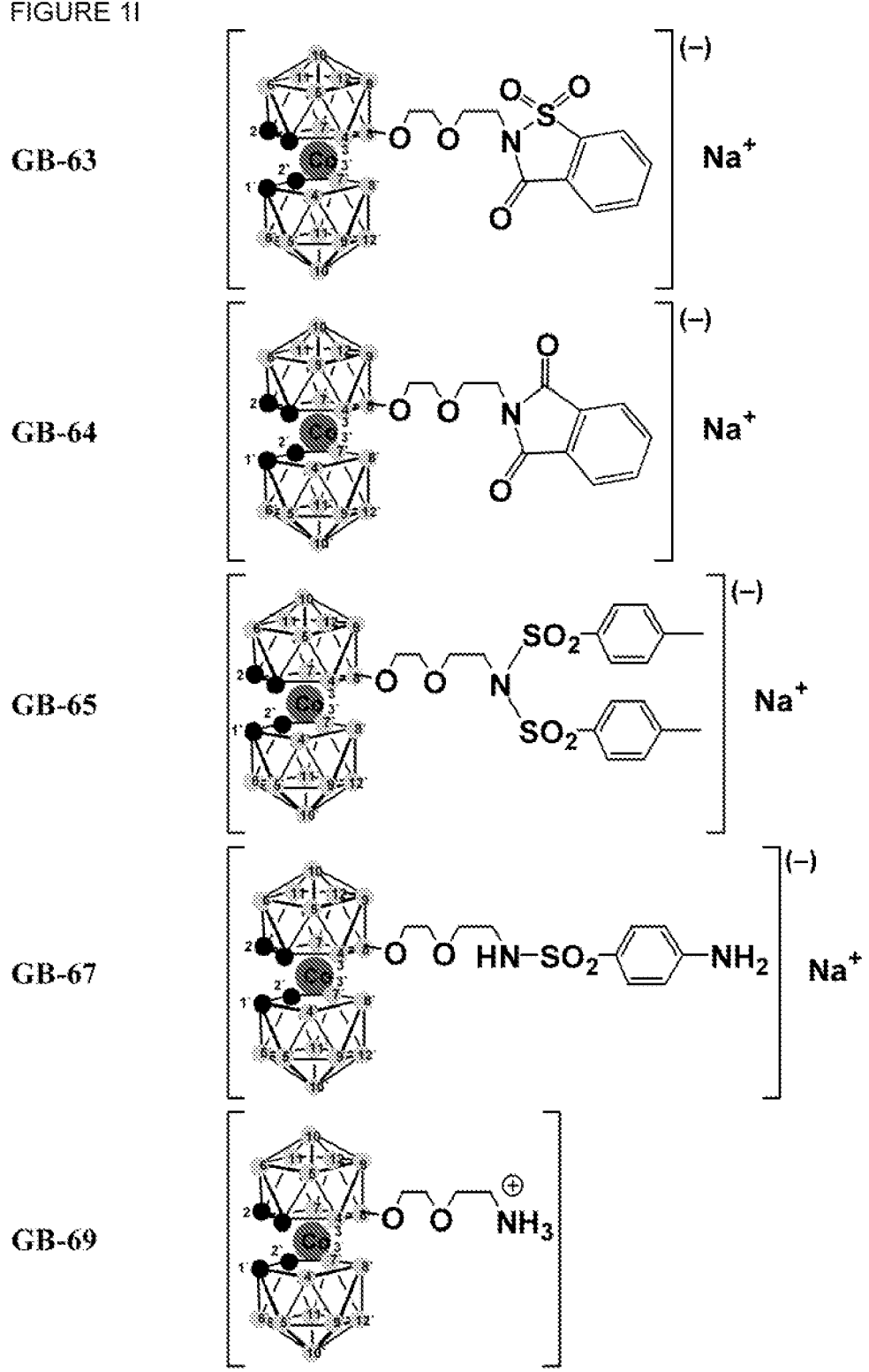
Figure 1J:
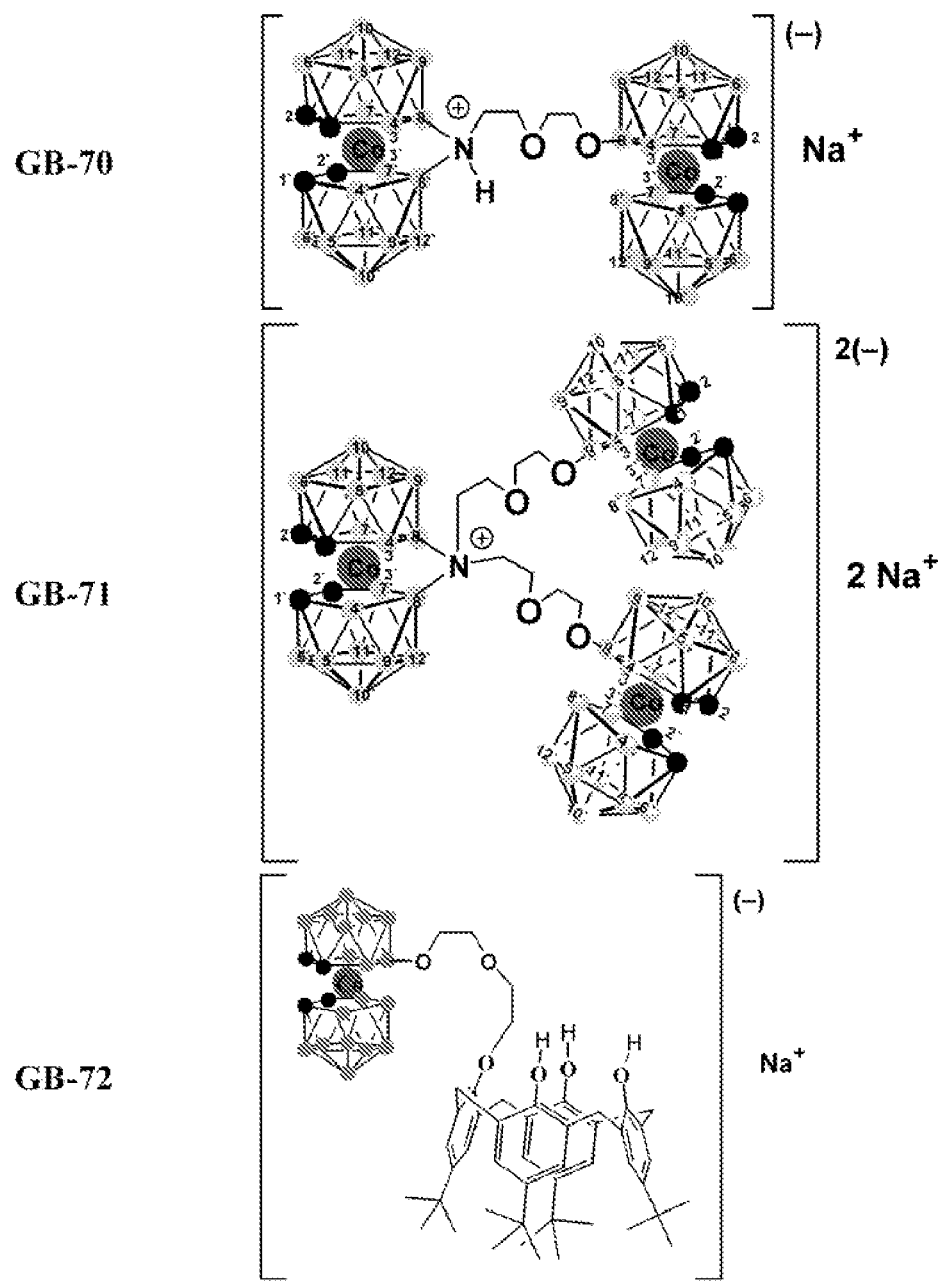
Figure 1K:
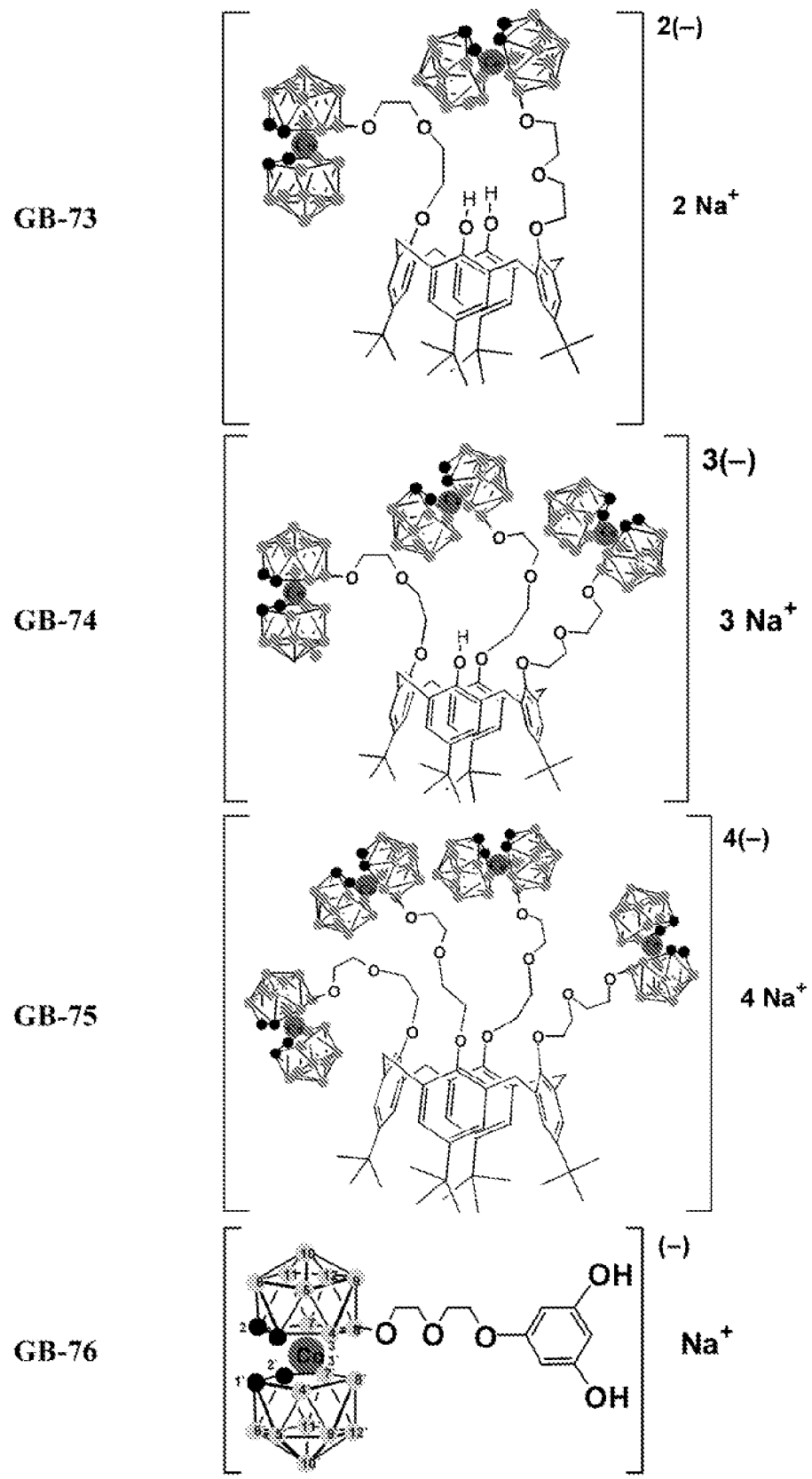
Figure 1L:
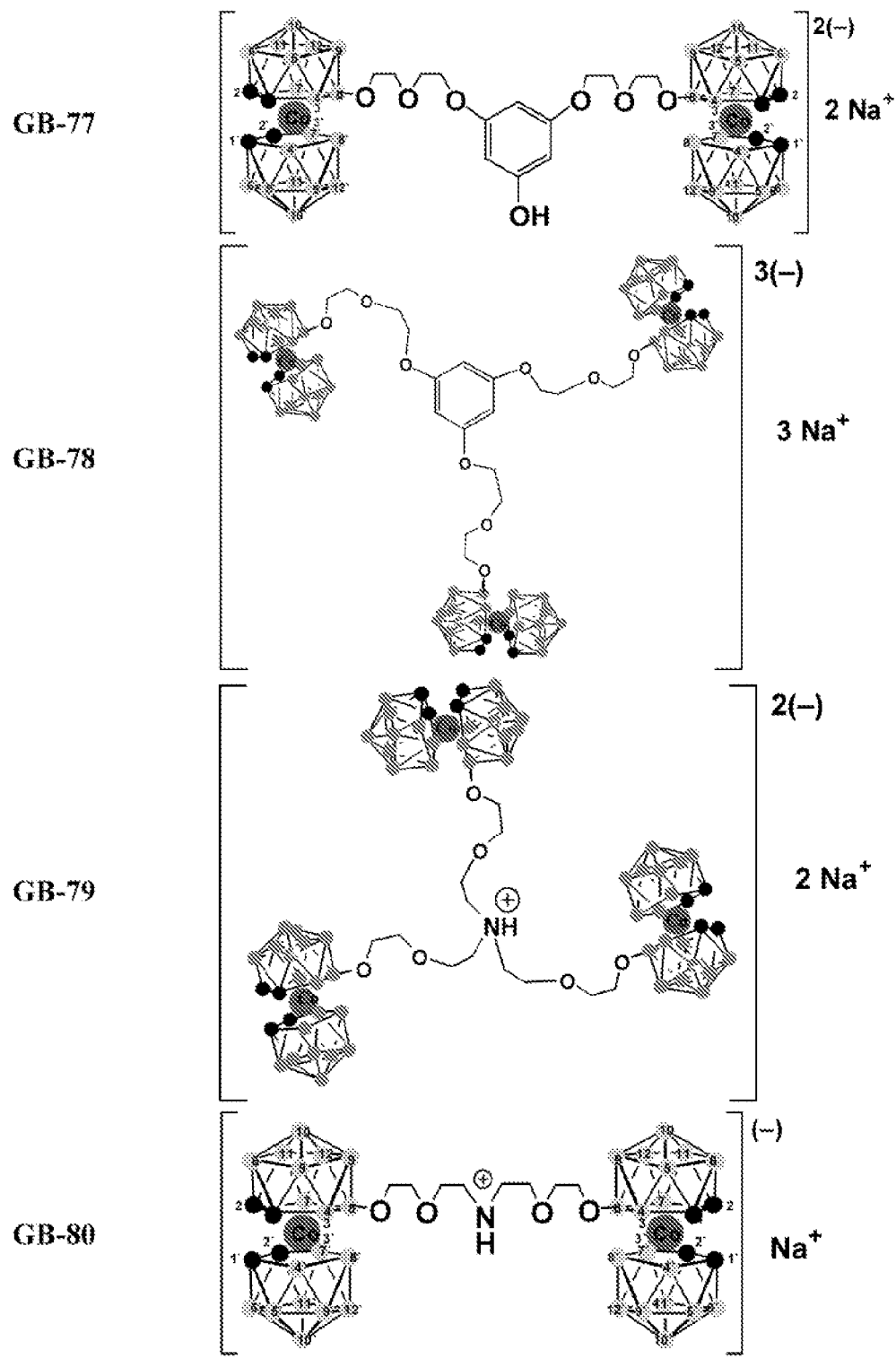
Figure 1M:
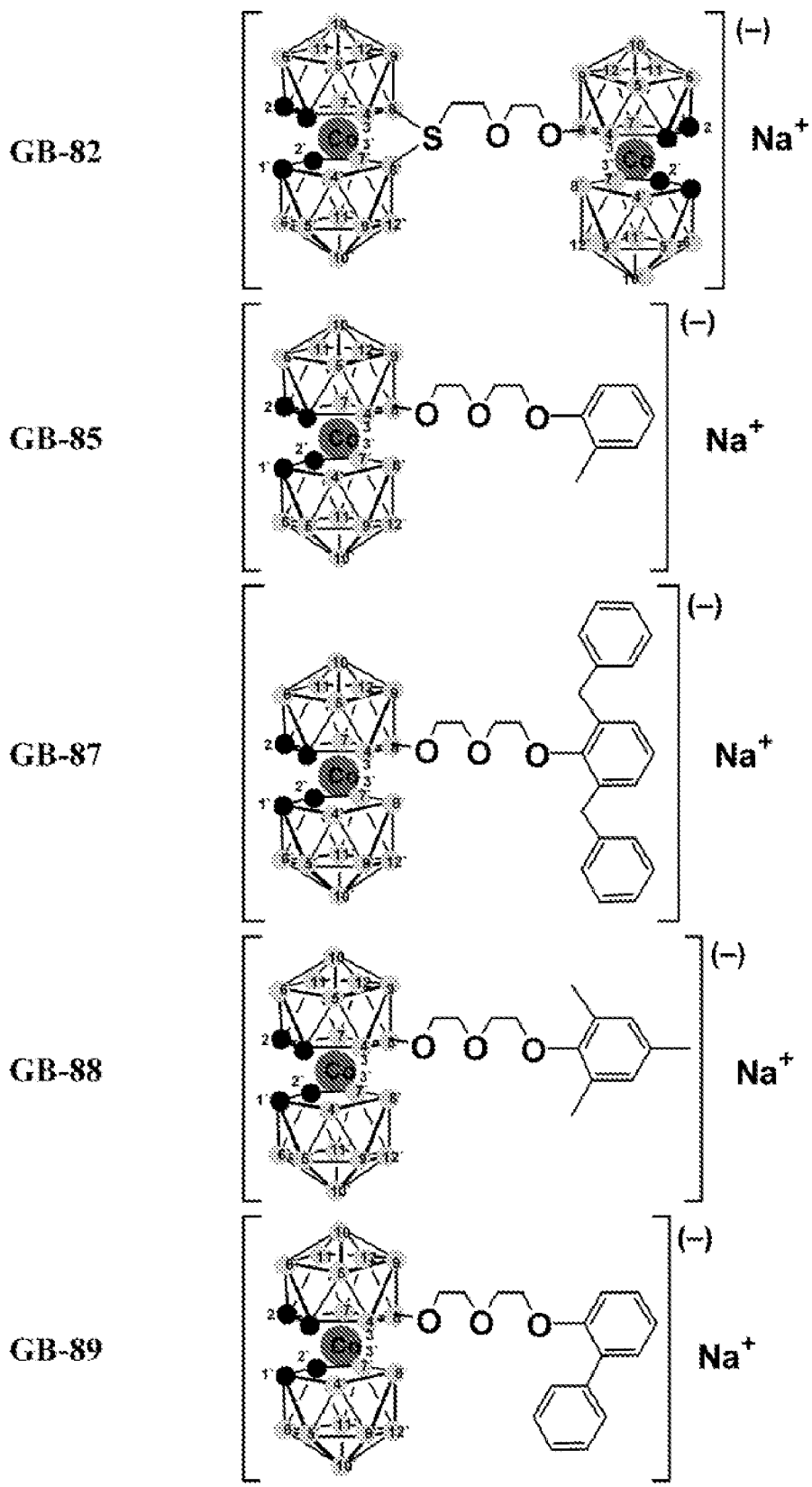
Figure 1N:
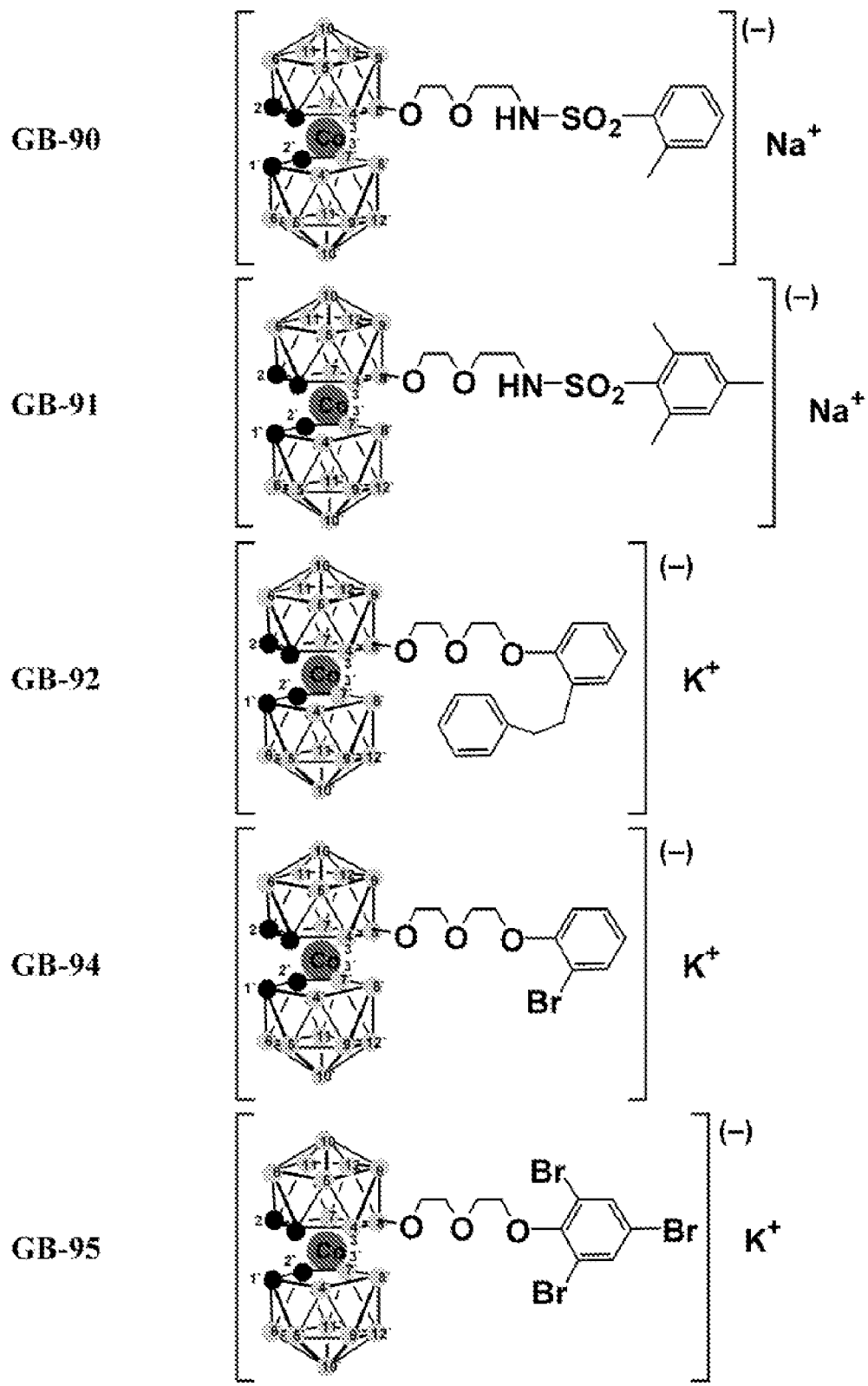
Figure 10:
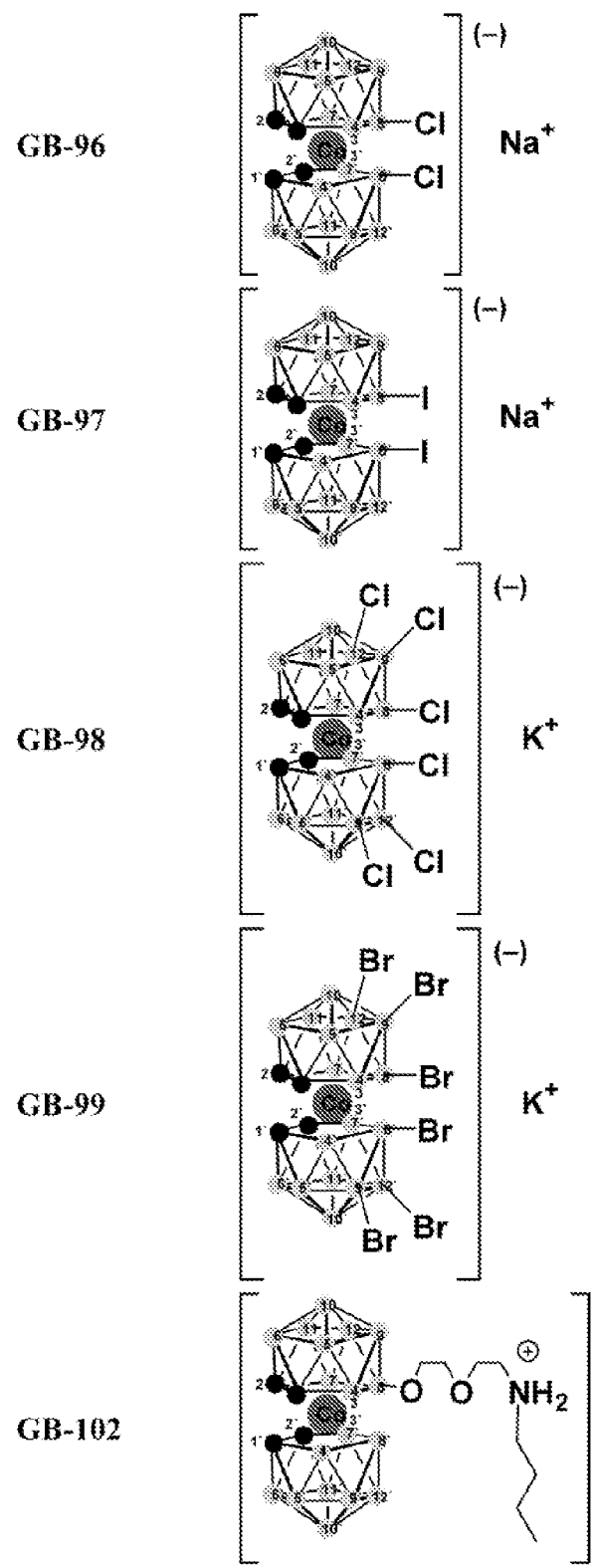
Figure 1P:
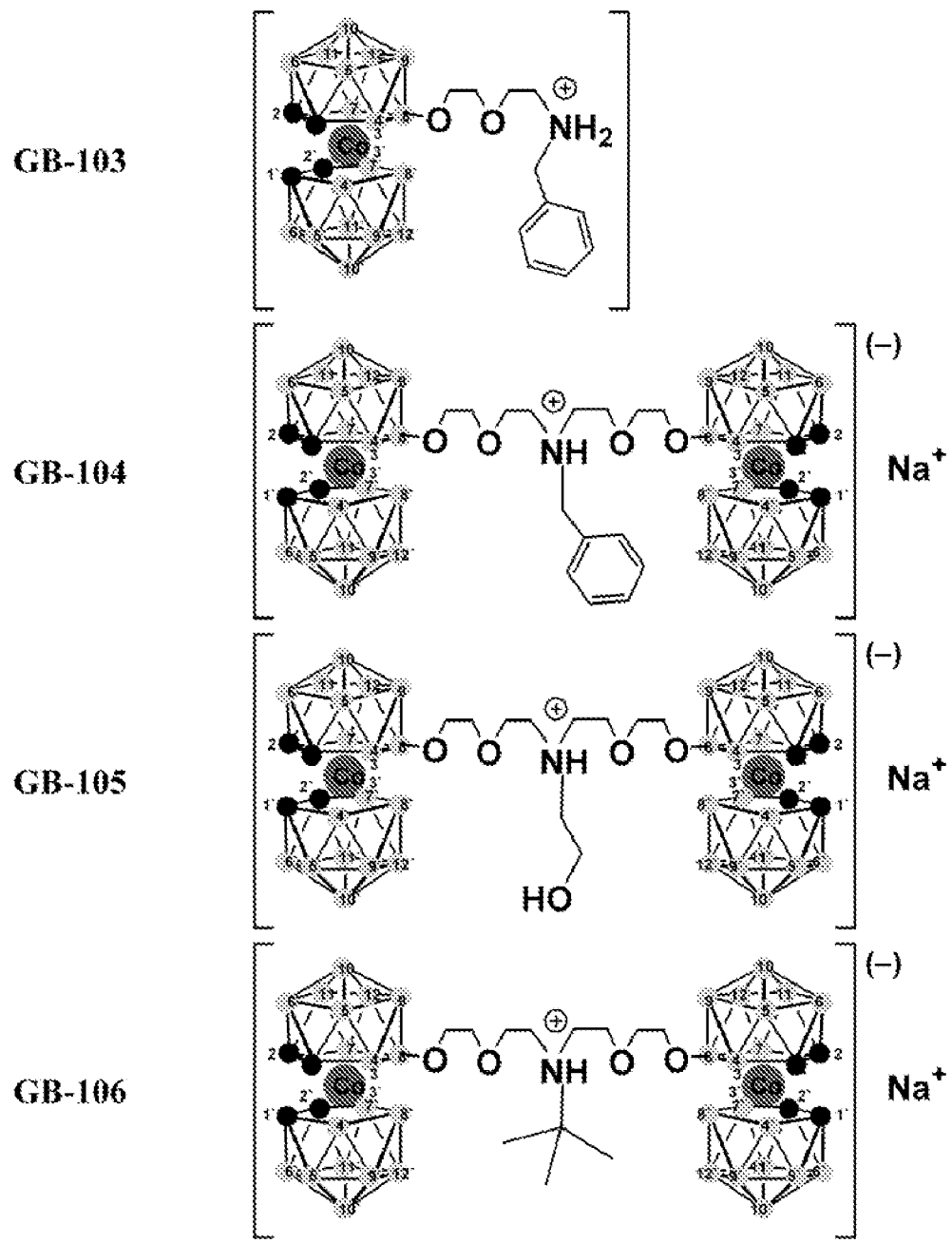
Figure 2:
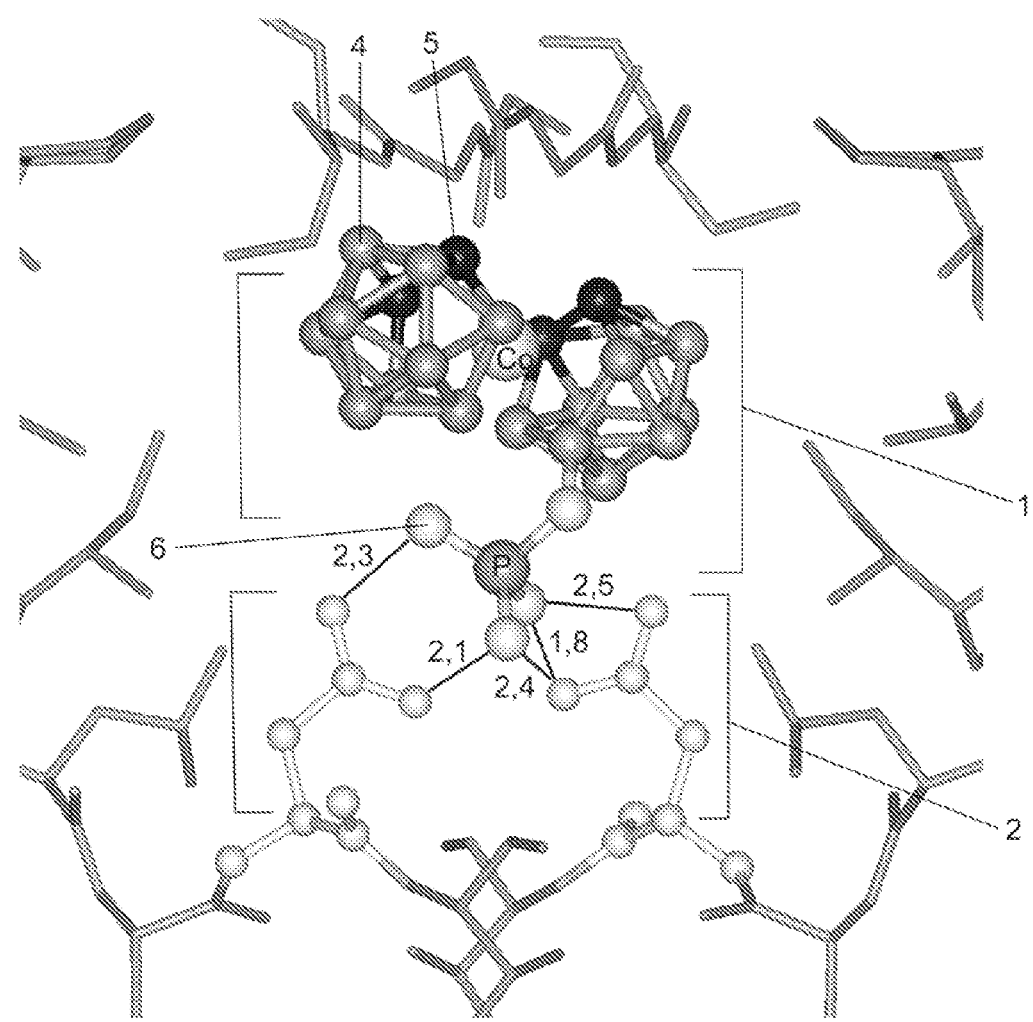
FIG. 2 shows the model of interaction of compound GB-16 with HIV-1 protease.

Results of the molecular modelling process show that compounds based on metallacarborane cluster fulfill the steric and size requirements for binding of inhibitor into the HIV protease active site. Furhermore, the structures of complexes of HIV protease and inhibitors show two remarkable advantages of the compounds of the invention. Firstly, from the distances measured between inhibitor oxygen atoms and protease oxygen atoms it is apparent that the functional groups of metallacarborane inhibitors can occupy such positions that enable creation of hydrogen bridging bonds with catalytic aspartates (FIG. 2). Secondly, remarkable surface complementarity between the HIV protease active site and metallacarborane inhibitor provides for strong hydrophobic interactions with the enzyme cavity (FIG. 3), which ensures strong bonding.

FIG. 2 shows model of interaction of GB-16 compound (1) with catalytic aspartates Asp25 and Asp25' (2), that are part of the HIV-1 protease active site. GB-16 inhibitor's atoms are shown as balls, sticks represent bonds between the atoms. Color labelling of GB-16 inhibitor atoms is as follows: black balls represent carbon atoms, grey balls represent boron atoms, white balls represent oxygen atoms, and phosphorus (P) and cobalt (Co) atoms are labelled with their symbols. Smaller white balls and white lines between them represent atoms and bonds that constitute catalytic aspartates Asp25 and Asp25'. Lines with numbers represent distances (in Ångström, 1 Ångström=0,1 nm) between oxygen atoms of catalytic aspartates and GB-16 inhibitor. The fact, that the distances do not exceed 2,5 Å, confirms that the positions of functional group of GB-16 inhibitor and catalytic aspartates are optimal for hydrogen bridging bonds creation. The HIV protease active site (with the exception of catalytic aspartates) is represented by stick model and colored in grey.

Figure 3:
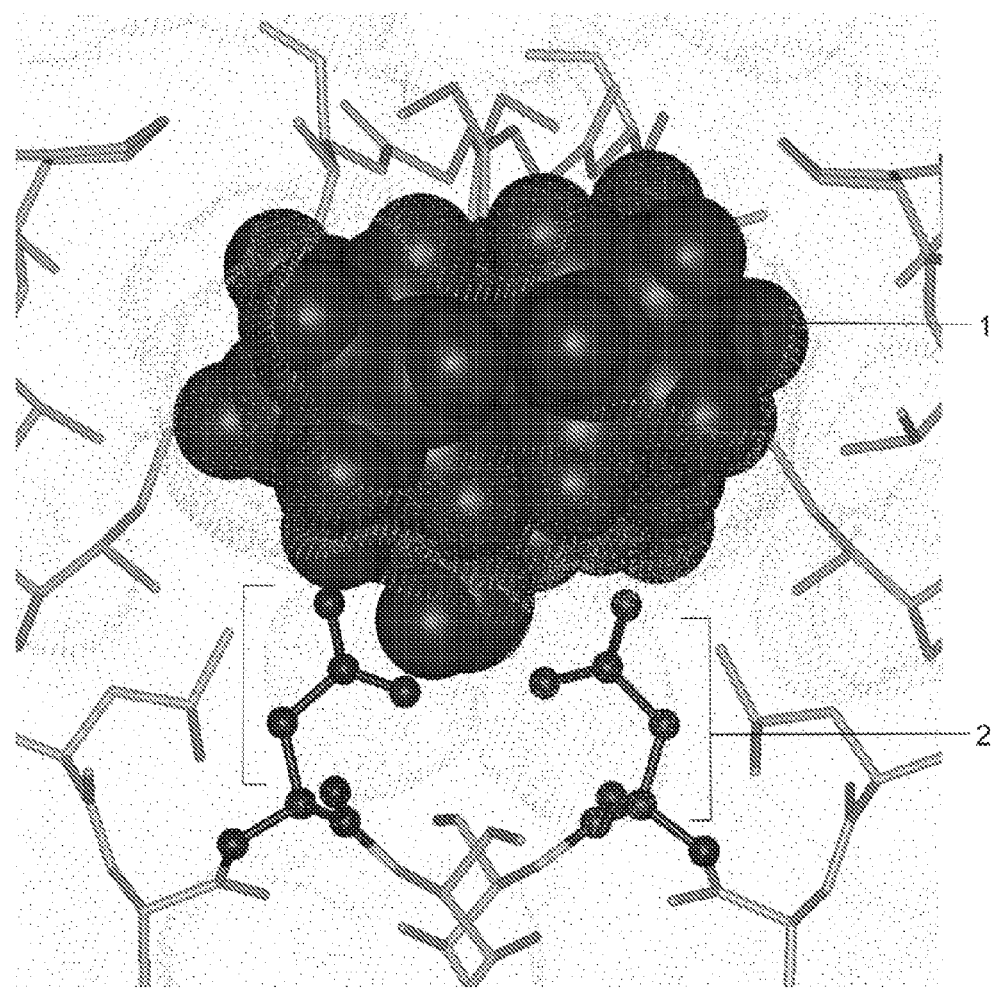
FIG. 3 shows the model of compound GB-24 inserted into the active site of HIV-1 protease.

FIG. 3 shows the model of GB-24 compound inserted into the HIV-1 protease active site. It can be seen that the inhibitor surface is highly complementary to the protease cavity. This close approach of mostly hydrophobic surfaces induces strong bonding between GB-24 inhibitor and HIV-1 protease. The van der Waals surface of the inhibitor (1) is represented by space-filling model (black), while the HIV protease cavity is represented as Connoly surface (grey points). Catalytic aspartates of HIV-1 protease Asp25 and Asp25' (2) are colored in black, while the rest of active site is colored in grey.

2. Syntheses of Novel Compounds

General method of syntHesis of novel compounds GB-21, GB-22, GB-25, GB-35, GB-40, GB-41, GB-43, GB-44, GB-45, GB-46, GB-48, GB-49, GB-50, GB-51, GB-52, GB-53, GB-54, GB-55, GB-56, GB-57, GB-58 GB-59, GB-60, GB-61, GB-63, GB-64, GB-65, GB-67, GB-70, GB-71, GB-76, GB-77, GB-78, GB-79, GB-80, GB-82, GB-85, GB-87, GB-88, GB-89, GB-90, GB-91, GB-92, GB-94, GB-95, GB-104, GB-105 and GB-106.

A compound L—Y—Z, or optionally L—Z (1.5 mmol), wherein L, Y and Z are as defined herein above, is added to a suspension of sodium hydride (80%, oil protected) (0.1 g, 3.3 mmol) in benzene (1.5 ml) and 1,2-dimethoxyethane (3 ml). 8-dioxane-cobalt bis(dicarbollide) (0.50 g, 1.22 mmol) or 8-tetrahydrofuran-cobalt bis(dicarbollide) (0.48 g, 1.22 mmol) is then added and the reaction mixture is heated to 70° C. The course of the reaction is monitored by thin layer chromatography, until the spot pertaining to the reacting cobalt bis(dicarbollide) disappears (Rf=0.6 on Silufol, $CHCl_3$ as an eluent). The reaction is usually completed in 5-10 min. After cooling to room temperature 10 ml of diethylether are added and the mixture is then filtered through paper filter which is subsequently washed with a few ml of ethanol (removing of residual NaH). The filtrate is evaporated in vacuum, 20 ml of water are added to the residue and approximately 2 ml of the suspension are evaporated to remove the residual solvents. The product is then extracted twice with dichloromethane (10 ml in total). In order to accelerate the phase separation sodium chloride should be added (0.2 g). The combined organic fractions are filtered through paper filter and checked by thin layer chromatography (Silufol, acetonitrile/chloroform 1:2 v/v). If only one spot is present, twofold amount of hexane is poured over the dichloromethane solution and the system is left to crystallize for at least two days. The product then appears in the form of crystals or in the form of a solid oil. In the latter case the supernatant is decanted from the oily layer, which is then converted into a brittle foam in vacuo at 50° C. (ca 15 min.).

In case that TLC of the original product shows more than one spot, the product is anchored in silica gel and the components of the mixture are separated by gradual elution of the mixture with acetonitrile/chloroform (1:2 v/v). After mobile phase evaporation the components are worked up as described herein above.

The yields of the preparation are almost quantitative with respect to the initial amount of cobalt bis(dicarbollide). Sodium salts usually crystallize with two molecules of water per one $Na^+$ cation.

For compounds GB-35, GB-46, GB-48, GB-50, GB-56, GB-57, GB-71, GB-77, GB-78, GB-79, GB-80, GB-104, GB-105 and GB-106 the procedure is repeated until the desired degree of substitution of reactive protons in polyols, polyphenols, amines, amides and sulfonamides is achieved. Compounds obtained by this procedure contain more than one cobalt bis(dicarbollide) cluster.

Characterisation of Compounds Prepared According to the General Method of Synthesis of Novel Compounds The compounds prepared by the method as described herein above have almost identical $^1H$ and $^{11}B$ NMR spectra of the molecule except for $^1H$ NMR signals of the Y—Z groups, or Z group. All the novel compounds were characterised by $^1H$ and $^{11}B$ NMR spektroscopy, the data can be summarized into general characteristics as described herein further.

In $^1H$ NMR spectra two $CH_{carborane}$ groups: 4.23 ppm (s, H) and 3.10 ppm (s,2H) are characteristic, as well as O—$CH_2CH_2$O—B group: 4.11-3.60 ppm (t, 2H) and 3.81-3.20 ppm (t, 2H), O—$CH_2CH_2$O— group: both $CH_2$-group resonate within the range 4.5-2.0 ppm (m, 4H). Hydration water: characteristic broad signal at ca 4.3 ppm.

$^{11}B$ NMR: Overlap of two sextets of signals with intensity ratios 1:1:2:2:2:1, i.e. theoretically 12 signals. 11 signals can be distinguished, two signals usually merge (e.g. at −22.1 ppm). Only the signal at ca 23 ppm is a singlet (corresponds to $B_{(8')}$—O—), the others are doublets. Exceptionally large range of the spectra (ca 52 ppm from +22.93 to −28.42 ppm) is determined by the range of the spectrum of the substituted dicarbollide ligand. The signals of unsubstituted dicarbollide ligand are within the smaller range (ca 22.5 ppm) and are only slightly shifted in comparison with signals of original cobalt bis(dicarbollide). On this basis, it is possible to distinguish them, but sometimes they are hidden in the substituted ligand spectrum.

As an example, it is demonstrated that:

GB-21

$^1H$ NMR: 400 MHz, acetone-$d_6$, 8.01 (s, 1H, HO—), 7.24-7.17 (m, 10H, overlaped 2 phenyl groups), 4.24 (broad s, 2H, $H_2O$), $CH_{carborane}$: 4.23 (s, H) and 3.10 (s, 2H), group O—$CH_2CH_2$O—B: 4.11 (t, 2H) and 3.81 (t, 2H), group O—$CH_2CH_2$O—: both $CH_2$ groups are overlaped: 3.64-3.59 (m, 4H).

$^{11}B$ NMR: (128 MHz) acetone-$d_6$: 23.92 s (2B, B8), 5.57 d (2B, B8'), 0.5 d (2B, B10'), −2.47 d (2B, B10), −4.6 d (4B, B4',7'), −6.92 d, −7.347 d (8B, B9, 12, 9',12'), −8.63 d (4B, B4, 7), −17.17 d (4B, B5', 11'), −20.21 d (4B, B5, 11), −21.97 d (2B, B6'), −28.44 d (2B, B6).

GB-22

$^1H$ NMR: 400 MHz, acetone-$d_6$, 7.33-7.24 (asym. m., 10 H, 2 Ph-groups), 3.78 (s, 2H, 2 CH groups), 2.65 (s, 8H, 2×2 $H_2O$), $CH_{carborane}$: 4.2 (s, H) and 3.1 (s, 2H), group O—$CH_2CH_2$O—B: 4.1 (t, 2H) and 3.8 (t, 2H), group O—$CH_2CH_2$O—: both $CH_2$ groups: 3.6 (m, 4H).

$^{11}B$ NMR: (128 MHz) acetone-$d_6$: 23.92 s (2B, B8), 5.57 d (2B, B8'), 0.5 d (2B, B10'), −2.47d (2B, B10), −4.6 d (4B, B4',7'), −6.92 d, −7.347 d (8B, B9, 12, 9',12'), −8.63 d (4B, B4, 7), −17.17 d (4B, B5', 11'), −20.21 d (4B, B5, 11), −21.97 d (2B, B6'), −28.44 d (2B, B6).

GB-25

$^1H$ {$^{11}B_{selective}$} NMR, 400 MHz, acetone-$d_6$: 4.15 (2H, $CH_{carborane}$), 4.104 (4H, $CH_{carborane}$) 3.790-3.712 m (12H, $CH_2$—O), 3.632 m (4H, $CH_2$—O), [2.95] (H10'), [2.89] (H4', 7'), [2.69] (H10), [2,61] (H8'), [2.058] (H9',12'), [1.846] (H4, 7, 9, 12), [1.73] (H6'), [1.622] (H5', 11'), [1.541] (H5. 11). [1,46] (H6).

$^{11}B$ NMR: (128 MHz) acetone-$d_6$: 23.92 s (2B, B8), 5.57 d (2B, B8'), 0.5 d (2B, B10'), −2.47 d (2B, B10), −4.6 d (4B, B4',7'), −6.92 d, −7.347 d (8B, B9, 12, 9',12'), −8.63 d (4B, B4, 7), −17.17 d (4B, B5', 11'), −20.21 d (4B, B5, 11), −21.97 d (2B, B6'), −28.44 d (2B, B6).

Synthesis of GB-19

[(1,2-$C_2B_9H_{11}$)-3,3'-Co-(1,2-$C_2B_8H_{10}$)-3"-Co-(1",2"-$C_2B_9H_{11}$)]$Cs_2$ (1 g, 13 mmol) prepared as described in Curchill A H, Reis J N, Francis J N, Hawthorne M F (1970) *J. Am. Chem. Soc.* 92, 4993-4994; St.Clair D, Zalkin A, Templeton D H. (1969) *Inorg. Chem.* 8, 2080-2086, was combined with 50 ml of 60% (w/w) $H_2SO_4$ and the suspension was heated to 125° C. (temperature of the bath) for 35 h until ca 90% of the monohydroxy derivative peak disappeared (the reaction course was monitored by HPLC using the method of hydrophobic borate anion analysis taught in Grüner B., Plzák Z.: *J. Chromatogr. A* (1997) 789, 497). After cooling the reaction mixture 150 ml of water were added and the products were extracted into diethylether (3×20 ml). To the combined ether layers water (20 ml) was added and ether was evaporated in vacuum. To the aqueous solution cesium chloride (1.0 g) in 10 ml of water was added and the resulting suspension was filtered off and air-dried. The solid substance was combined with water (15 ml) and the suspension was heated in water bath at 85° C. Ethanol was added until the solid phase dissolved. The precipitated crystals were filtered off and dried in vacuum, redissolved in the mixture of solvents $CH_3CN$—$CH_2Cl_2$ 1:2 and chromatographed by low-pressure chromatography on a Merck 60 μm column in mobile phase $CH_3CN$—$CH_2Cl_2$ 1:2 with gradient until 1:1. After evaporation of solvents the solid phase was dissolved in hot mixture ethanol-water (1:1), CsCl (500 mg) was added and the solution was left to cool to room temperature and to crystallize for 2 days. Dark red crystals were filtered off and recrystallized from the ethanol-water mixture.

Yield: 390 mg (37%) of unsymmetrically substituted isomer, 105 mg (10.1%) of the isomer symmetrically substituted at the central cluster.

Symmetrical isomer: $^1H$ {$^{11}B_{selective}$}NMR: 400 MHz, acetone-$d_6$, 3.564 (4H, $CH_{carborane}$), 3.336 (2H, $CH_{carborane}$), [3.288] (BH), [2.775] (BH), [2.593] (BH), [2.406] (BH), [1.737] (BH), [1.740] (BH), [1.631] (BH), [1.550] (BH), [1.424] (BH).

$^{11}B$ NMR: (128 MHz) acetone-$d_6$: 28.28 d (2B), 4.59d (2B), −2.23 d (4B), −4.16 d (2B), −7.85 d (8B), −8.89 d (2B), −18.98 d (4B), −22.92 d (2B).

Dicesium salt was converted into disodium salt (GB-19) by the following procedure: 100 mg of the salt was shaked between 3M HCl (10 ml) and diethylether (10 ml), the organic layer was separated and shaked twice with 3M HCl (10 ml). The organic phase was shaked three times gradually with 20 ml of 10% aqueous solution of $Na_2CO_3$, 20 ml of water, the ether phase was separated and evaporated and dried at 80° C. in vacuum.

Synthesis of GB-24

Twice 150 mg (0.44 mmol) of amino derivative [(1,2-$C_2B_9H_{10}$)-3,3'-Co(1',2'-$C_2B_9H_{10}$)-8,8'-μ-NH], prepared as taught in the work (Plešek J, Heřmánek S, Baše K, Todd L J, F. W W. (1976) *Collection Czechoslovak. Chem. Commun.* 41, 3509-3515; Plešek J, Rajabi F H, Vangani V, Fusek J. (1994) *Collection Czechoslovak. Chem. Commun.* 59, 1326-1336) were dissolved in diethyleneglycol dimethylether (DME) (15 ml) in two flasks and to both solutions 12 mg of sodium hydride having large specific surface ($2\ m^2g^{-1}$) were added under stirring in dry nitrogen atmosphere. The reaction mixture in flask A was stirred 1 h at ambient temperature, then 35 μl of epichlorohydrin were added through septum and the reaction mixture was stirred 2 h at ambient temperature. Content of flask B was added by cannula to the flask A. The reaction mixture was stirred 2 h at ambient temperature and then 26 h at reflux. After cooling down the reaction mixture, silica gel for chromatography (Merck, 2 g) was added into the flask and the solvent was evaporated. Silica gel covered with reaction products was transferred to silica gel column (2×25 cm) and the products were eluted with benzene-hexane 2:1 mixture until the unreacted reactant was washed out and then with benzene.

The solution containing compound corresponding to the red spot in TLC (Silufol, benzen) with $R_F$=0.37 was collected. The solution was evaporated and the product was purified by silica gel chromatography.

Yield: 105 mg (32%).

$^1H$ NMR, 400 MHz, acetone-$d_6$, 7.41 (2H, NH), 4.791 (2H, $CH_2$), 4.241 (2H, CH) 3.296 (8H, $CH_{carborane}$).

$^{11}B$ NMR, 128 MHz, acetone-$d_6$: 5.044 s (4B), −1.021 d (4B), −8.66 d, −9.891 d, −11.15 d (16B), −15.77 d (8B), −25.59 d (4B).

3. Synthesis of Known Compounds

GB-1

The compound was prepared by the reaction of established neutral compound, 8-dioxan-cobalt bis(dicarbollide) derivative (Plešek J, Heřmánek S, Franken A, Císařová I, Nachtigal C. (1997) *Collection Czechoslovak. Chem. Commun.* 62, 47-56) with sodium hydroxide in aqueous dioxane were the following procedure: 1.0 g of 8-dioxan-cobalt bis(dicarbollide) was dissolved in 50 ml of dioxan-water mixture 4:6 and 10 ml of 10% sodium hydroxide solution were added. The reaction mixture was heated to 80° C. for two hours. After cooling down the mixture, 100 ml of water were added, dioxane was evaporated at low temperature and then 50 ml of 3M HCl were added. The aqueous phase was extracted with diethylether (3×30 ml). The combined organic layers were washed with water (2×20 ml) and separated. After addition of 50 ml of water, ether was evaporated. Ethanol was added until the dissolution of the product and the product was then precipitated by excess aqueous $(CH_3)_3N.HCl$, filtered and dried in vacuum.

Yield of (8-HO—$(CH_2$—$CH_2O)_2$-1,2-$C_2B_9H_{10}$)(1',2'-$C_2B_9H_{11}$)-3,3'-Co]$(CH_3)_3$NH: 0.99 g, 86%.

$^1H$ NMR: acetone-$d_6$, 4.27 (2H, $CH_{carborane}$), 4.11m (2H, $CH_2$—O), 3.97s (2H, $CH_2$), 3.81 (2H, $CH_2$—O), 3.64-3.59 m (4H, $2CH_2$—O), 3.10s (2H, $2CH_{carborane}$), [2.95] (H10'), [2.79] (H4',7'), [2.72] (H10), 2.90 (9H, $(CH_3)_3NH$, [2.48] (H8'), [2.06] (H9',12'), [2.06, 1.81] (H4, 7, 9, 12), [1.73] (H6'), [1.68] (H5', 11'), [1.59] (H5, 11), [1.49] (H6). $^{11}B$ NMR: acetone-$d_6$: 23.8s (B8), 5.2 (B8') (131), 0.5 (B10') (135), −2.5 (B10) (139), −4.6 (B4',7') (142), −7.0d, −7.5d (B9, 12, 9',12') (overlap), −8.7 (B4, 7) (176), −17.2 (B5', 11') (150), −20.3 (B5, 11) (150), −22.1d (B6') (overlap), −28.5 (B6) (135). M.S. m/z=415.3.

Analysis: % B calculated: 41.22, found: 40.84, % Co calculated: 12.49, found: 12.33.

Triethylammonium salt was converted into sodium salt by the following process: 1 g of the salt was shaked between 3M HCl (50 ml) and diethylether (30 ml), organic phase was separated and washed twice with 3M HCl (50 ml). The organic layer was then washed three times with 50 ml of 10% aqueous $Na_2CO_3$, 50 ml of water, the ether phase was separated and evaporated to dryness. The product was dried in vacuum.

In the literature, there can be found preparation of this compound by different, more complicated method (Sivaev I B, Starikova Z A, Sjoberg S, Bregadze V I. (2002) *J. Organomet. Chem.* 649, 1-8).

GB-8

The compound was prepared by direct hydroxylation of cobalt bis(dicarbollide) anion with diluted $H_2SO_4$ at higher temperatures, by the process taught in the literature (Plešek J, Grüner B, Báča J, Fusek J, Císařová I. (2002) *J. Organometal. Chem.* 649, 181-190).

GB-12

The bridging derivative of cobalt bis(dicarbollide) was prepared on the basis of known processes by the reaction of unsubstituted ion with paraformaldehyde (Plešek J, Heřmánek S, Baše K, Todd L J, F. W W. (1976) *Collection Czechoslovak. Chem. Commun.* 41, 3509-3515).

GB-16

The compound was prepared by the reaction of the above mentioned compound GB-8 with phosphorylchloride and subsequent hydrolysis of the intermediate as taught previously in the literature (Plešek J, Grüner B, Cisařová I, Báča J, Selucký P, Rais J. (2002) *J. Organometal. Chem.* 657, 59-70).

GB-23

The compound was prepared by the process taught in the literature (Hawthorne M F, Young D C, Wegner P A (1965) *J. Am. Chem. Soc.* 87, 1818).

GB-26 and GB-27

The compounds were prepared by the reaction of benzene with cobalt bis(dicarbollide) at higher temperature catalysed by $AlCl_3$, by the process taught in the literature (Plesek J., Hermanek S. (1995) Coll. Czech. Chem. Commun. 60, 1297-1302).

GB-28, GB-29 and GB-30

The compounds were prepared by the reaction of biphenyl (in case of GB-28), toluene (in case of GB-29) and 1,2-dimethylbenzene (in case of GB-30) with cobalt bis(dicarbollide) at higher temperature catalysed by $AlCl_3$, by the process taught in the literature (Teixidor F., Casensky B., Dozol J. F., Hermanek S., Mongeot H., Rais J. (1998) Report EC, EUR 18217 EN, Louxemburg).

GB-31

[(1,2-$C_2B_9H_{11}$)-3,3'-Co-(1,2-$C_2B_8H_{10}$)-3"Co-(1",2"-$C_2B_9H_{11}$)]$Cs_2$ was prepared by the reaction of [$(C_2B_9H_{11})_2$Co]$^-$ with excess of $CoCl_2$ at strongly basic conditions by the process taught in the literature (J. N. Francis and M. F. Hawthorne (1968) *J. Amer. Chem. Soc.*, 90, 1663-1664; St.Clair D, Zalkin A, Templeton D H. (1969) *Inorg. Chem.* 10, 2080-2086) a preveden na sodnou s ů podle popsané procedury (Plesek J., Base K., Mares F., Hanousek F., Stibr B. and Hermanek S. (1984): Coll. Czech. Chem. Commun. 49, 2776-2789).

GB-69

The compound was prepared from 8-dioxan-cobalt bis(dicarbollide) as taught previously in the literature (Sivaev I. B., Starikova Z. A., Sjöberg S., Bregadze V. I. (2002) *J. Organomet. Chem.* 649, 1-8).

GB-72, GB-73, GB-74 and GB-75

The compounds were prepared by the reaction of calix[4]arene with 8-dioxan-cobalt bis(dicarbollide) by the process taught in the literature (Gruner B., Mikulasek L., Baca J., Cisarova I., Bohmer V., Danila C., Reinoso-Garcia M., Verboom W., Reinhoudt D. N., Casnati A, Ungaro R. (2005) *Eur J. Org. Chem.*, 10, 2022-2039).

GB-96, GB-97, GB-98 and 99

The compounds were prepared by direct halogenation of cobalt bis(dicarbollide) by the process taught in the literature (Matel J., Macasek F., Rajec P, Hermanek S., Plesek J. (1982) *Polyhedron* 1, 511-519).

GB-102, GB-103

The compounds were prepared by the reaction of butylamine or benzylamine, respectively, with 8-dioxan-cobalt bis(dicarbollide) by the process taught in the literature (Gruner B. et al. (2002) *New J. Chem.* 26, 1519-1527).

4. Testing of Potency of Known and Novel Compounds In Vitro

Initially, known and novel compounds were tested as to their ability to inhibit specific activitity of HIV protease in vitro using pure recombinant HIV protease and chromogenic peptide substrate derived from amino acid sequence of one of the sites of cleavage of viral polyprotein. Testing was performed using the method published by one of the co-inventors of this invention (Konvalinka, J., Litera, J., Weber, J., Vondrásek, J., Hradilek, M., Souček, M., Pichová, I., Majer, P., Strop, P., Sedláček, J., Heuser, A. -M., Kottler, H. and Kraeusslich, H. -G. (1997). *Eur. J. Biochem.* 250, 559-566). In a typical experiment various amounts of the inhibitor to be tested dissolved in DMSO (in such a way that the final concentration of DMSO did not exceed 2.5%) were added to pure recombinant 8 nM HIV protease in 1 ml of acetate buffer (pH 4.7) containing 0.3 M sodium chloride and the reaction was initiated by addition of chromogenic substrate of the sequence KARVNleF(NO$_2$)EANle-NH$_2$ (wherein Nle represents norleucine and F(NO$_2$) is para-nitrophenylalanine) until the final concentration of 15 µM. The reaction course is observed spectrophotometrically as decrease of the absorbance at 305 nm. IC$_{50}$ values of tested compounds were calculated from experimental data, as taught in (Majer, P., Urban, J., Gregorová, E., Konvalinka, J., Novek, P., Stehlíková, J., Andreánsky, M., Sedláček, J. and Strop, P. (1993) *Arch.Biochem.Biophys.* 304, 1-8) and are shown in Table 1.

Inhibition testing of GB-16 was performed also for wild type HIV-2 protease, mutant HIV-1 PR 3/1 and cathepsin D. Results are shown in Table 2.

Furthermore, selected new compounds GB-48 and GB-80 were tested for their ability to inhibit resistant variants of HIV-1 proteases. Table 3 shows inhibition constants (Ki values) for the clinically used inhibitors saquinavir, indinavir and for compounds GB-48 and GB-80. All three proteases bind saquinavir and indinavir far worse than wild-type HIV-1 protease. It is obvious that the binding affinity of GB-48 and GB-80 to resistant HIV proteases is comparable with their affinity to wild-type hence GB-48 and GB-80 keep their potency against several resistant HIV-1 proteases in comparison with clinically used inhibitors.

Figure 4:
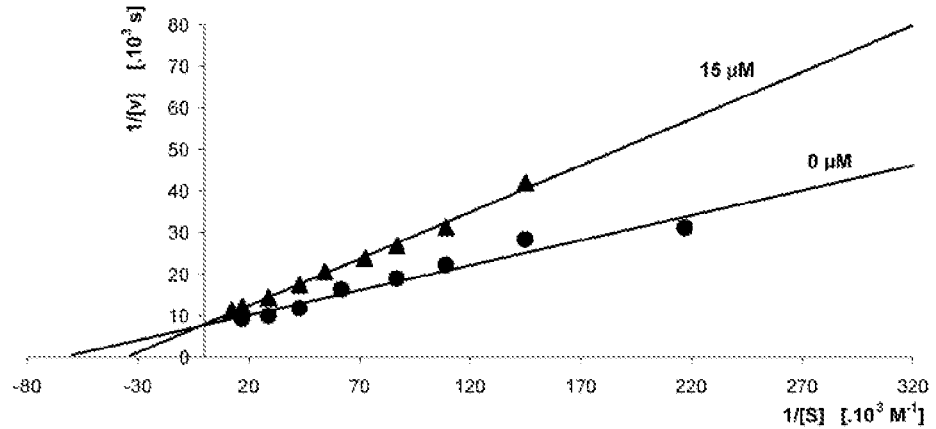
FIG. 4 represents graphically the dependence of enzyme reaction rate on substrate concentration in presence of inhibitor GB-16.

The mechanism of action of tested compounds (inhibition type) were determined from dependence of initial reaction rate on substrate concentration at different inhibitor concentrations (Lineweaver-Burke plot). Example of determining the mechanism of action of GB-16 inhibitor by the Lineweaver-Burke plot is shown in FIG. 4. Dependence of initial enzyme reaction rate on substrate concentration is measured at various inhibitor concentrations (here 0 and 15 µM). The measurements were performed at pH 4.7, 37° C. in 0.1 M acetate buffer containing 0.3M NaCl. y axis: reciprocal value of initial enzyme reaction rate, x axis: reciprocal value of substrate concentration (mol/dm$^3$). The GB-16 inhibitor is a competitive inhibitor.

TABLE 1

IC$_{50}$ values of particular inhibitors determined for wild type HIV-1 protease.

| Inhibitor | IC$_{50}$ |
|---|---|
| GB-1 | 6.1 µM |
| GB-8 | 13.5 µM |
| GB-12 | 5.2 µM |
| GB-16 | 6.2 µM |
| GB-18 | 1.1 µM |
| GB-19 | 1.8 µM |
| GB-21 | 130 nM |
| GB-22 | 50 nM |
| GB-23 | 550 nM |
| GB-24 | 160 nM |
| GB-25 | 60 nM |
| GB-26 | 0.93 µM |
| GB-27 | 1.6 µM |
| GB-28 | 290 nM |
| GB-29 | 1.2 µM |
| GB-30 | 680 nM |
| GB-31 | 100 nM |
| GB-35 | 200 nM |
| GB-40 | 1.2 µM |
| GB-41 | 660 nM |
| GB-42 | 100 nM |
| GB-43 | 210 nM |
| GB-44 | 270 nM |
| GB-45 | 160 nM |
| GB-46 | 50 nM |
| GB-47 | 640 nM |
| GB-48 | 100 nM |
| GB-49 | 220 nM |
| GB-50 | 160 nM |
| GB-51 | 130 nM |
| GB-52 | 190 nM |
| GB-53 | 180 nM |
| GB-54 | 200 nM |
| GB-55 | 120 nM |
| GB-56 | 60 nM |
| GB-57 | 70 nM |
| GB-58 | 160 nM |
| GB-59 | 240 nM |
| GB-60 | 260 nM |
| GB-61 | 340 nM |
| GB-63 | 130 nM |
| GB-64 | 840 nM |
| GB-65 | 120 nM |
| GB-67 | 200 nM |
| GB-69 | 2.2 µM |
| GB-70 | 230 nM |
| GB-71 | 250 nM |
| GB-72 | 210 nM |
| GB-73 | 110 nM |
| GB-74 | 100 nM |
| GB-75 | 91 nM |
| GB-76 | 2.3 µM |
| GB-77 | 100 nM |
| GB-78 | 120 nM |
| GB-79 | 130 nM |
| GB-80 | 140 nM |
| GB-82 | 230 nM |
| GB-85 | 710 nM |
| GB-87 | 260 nM |
| GB-88 | 240 nM |
| GB-89 | 300 nM |
| GB-90 | 230 nM |

TABLE 1-continued

IC$_{50}$ values of particular inhibitors determined for wild type HIV-1 protease.

| Inhibitor | IC$_{50}$ |
|---|---|
| GB-91 | 210 nM |
| GB-92 | 170 nM |
| GB-94 | 170 nM |
| GB-95 | 120 nM |
| GB-96 | 1.08 μM |
| GB-97 | 870 nM |
| GB-98 | 1.03 μM |
| GB-99 | 690 nM |
| GB-102 | 2.2 μM |
| GB-103 | 1.4 μM |
| GB-104 | 140 nM |
| GB-105 | 140 nM |
| GB-106 | 130 nM |

TABLE 2

K$_i$ and IC$_{50}$ values for inhibitor GB-16 and various proteases (PR).

| Recombinant protease type | IC$_{50}$ | K$_i$ |
|---|---|---|
| wild-type HIV-1 PR | 6.2 μM | 16.3 μM |
| wild-type HIV-2 PR | 15.4 μM | 7.4 μM |
| HIV-1 PR 3/1 | 13.4 μM | 3.6 μM |
| cathepsin D | 32.9 μM | 17.2 μM |

TABLE 3

Inhibition constants Ki [nM] for wild-type and resistant HIV proteases and clinically used inhibitors saquinavir, indinavir and two selected compounds GB-48 and GB-80.

| Typ of HIV protease | Mutation | SQV | IDV | GB-48 | GB-80 |
|---|---|---|---|---|---|
| wild type | — | 0.04 | 0.12 | 2.2 | 4.9 |
| HIV PR 15 | M46I, A71V, V82T, I84V | 13 | 21 | 9.0 | 22 |
| HIV PR K4 | L10I, L24I, L33F, M46L, I54V, L63P, A71V, V82A, I84V | 180 | 35 | 24 | 13 |
| HIV PR 5/1 | L10I, I15V, E35D, N37S, R41K, I62V, L63P, A71V, G73S, L90M | 2.9 | 5.5 | 4.6 | 40 |

5. Testing of HIV Virus Infectivity Inhibition in Tissue Cultures

The antiviral activity of compounds GB-8, GB-12 and GB-16 in tissue cultures was analyzed using two variations of a published procedure (Benyoucef S, Hober D, Shen L, Ajana F, Gerard Y, Bocket-Mouton L, Mouton Y, Wattre P. (1996) *Microbiol Immunol.* 40(5), 381-8). The production of infectious HIV particles and influences of HIV protease inhibitors on the infectivity was directly determined by these assays.

For testing of compounds GB-8, GB-12 and GB-16, HeLa cells were transfected by DNA encoding pNL-43 strain of HIV virus that contained beta-galactosidase gene in the site of viral nef gene. All transfections were performed in duplicate. Medium was replaced the next day following the transfection, and protease inhibitors dissolved in DMSO were added into fresh medium. The control was incubated in the same DMSO concentration as tested cells. The supernatant of transfected cells was used in next round for reporter cells infection. Infectivity was quantified by enzyme beta-galactosidase activity in infected cells and the infected cells were visualised using chromogenic beta-galactosidase substrate (X-gal). Viral proteins of newly created virions were separated by SDS PAGE and immunochemically visualised using antibodies against HIV capsid protein (Western blot).

Figure 5:
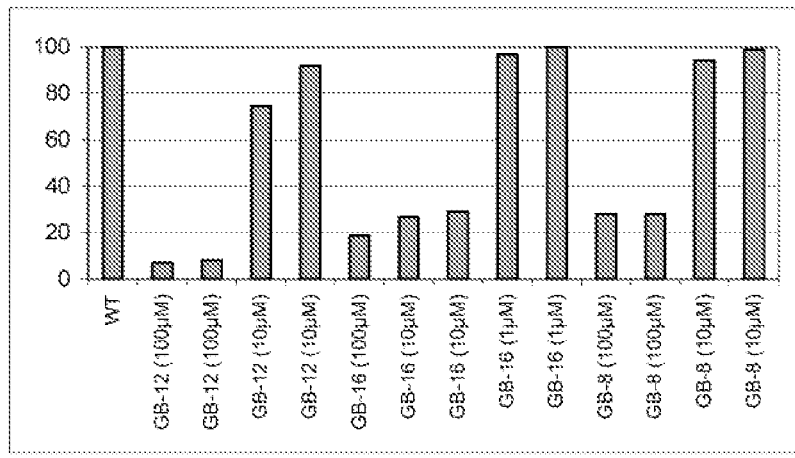
FIG. 5 represents the inhibition effect of GB-8, GB-12 and GB-16 inhibitors in tissue cultures transfected with proviral clone NL4-3.

In paralel experiments, HIV was produced in 293 T cells transfected by proviral clone NL 4-3. All transfections were performed in duplicate. Medium was replaced the next day following the transfection, and protease inhibitors dissolved in DMSO were added into fresh medium. The control was incubated in the same DMSO concentration as tested cells. Viral infectivity was quantified by titration of the cell supernatant by TZM cell (reporter cells bearing in their genome LTR promotor from HIV bound with beta-galactosidase gene, activated by Tat protein produced by the virus). After two days following the infection the reporter cells were lysed and fixed by methanol/acetone mixture. Beta-galactosidase activity of infected cells was visualised by blue color after chromogenic substrate X-gal addition. Result of typical experiment is shown in FIG. 5. The experiment proves that GB-8, GB-12 a GB-16 inhibitors block the virus infectivity. 10 μM solution of GB-16 inhibitor decreases HIV infectivity to ca 27% of the initial value; 100 μM solution of GB-8 inhibitor was needed to reach similar activity.

Figure 6:
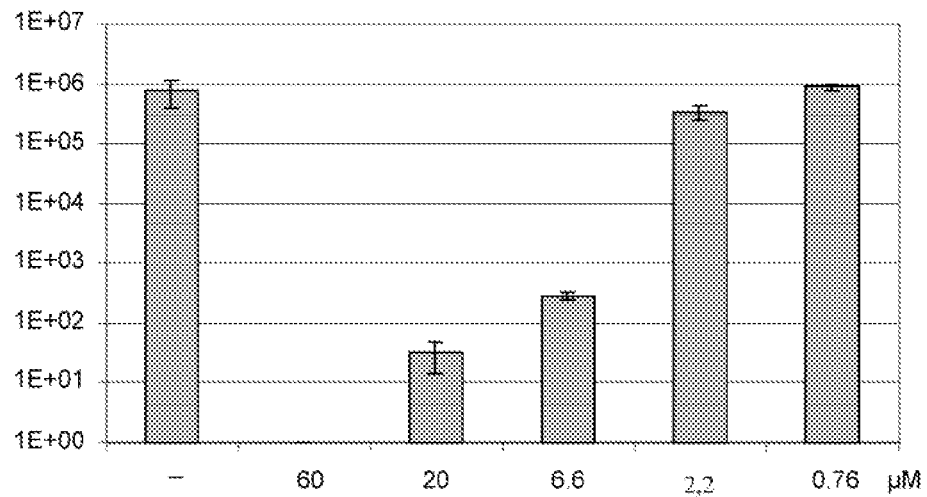
FIG. 6 represents the inhibition effect of GB-48 inhibitor in tissue cultures transfected with proviral clone NL4-3.

For testing of compound GB-48, PM1 cell cultures infected by virus strain NL4-3 were split 2 days post infection 1 to 10 with fresh, uninfected cells. To remove unbound virus cells were washed with pre-warmed medium four hours post infection. Cells were subsequently incubated for 40 h with a GB-48 dissolved in DMSO at a final concentration from 0.74 to 60 μM. Control cells were incubated with the same amount of DMSO as the GB-48 treated cells. To harvest the free virus cells were centrifuged at 1500 rpm for 5 min and 10 μl of the supernatants were used for titration. Changes in viral infectivity were analysed by titration of the supernatants on TZM-cells as described above. Two days post infection TZM-cells were lysed and fixed with methanol/aceton. The beta-galactosidase activity of infected cells was visualised by blue stain upon X-Gal addition. All titrations were done in duplicate assays. The viral titer and standard deviation was calculated from three independent titrations. Example of the activity testing is given on FIG. 6. GB-48 strongly inhibited virus infectivity at concentrations of 6,6 to 60 μM. At these concentrations drops in viral titer of at least 3 orders of magnitude in virus infectivity were observed.

INDUSTRIAL APPLICABILITY

The invention is applicable in pharmaceutical industry and in medicine for the treatment of patients infected by HIV and for the treatment of AIDS.

We claim:

1. A HIV protease inhibitor composition comprising a compound of formula:

A—Z—(CH$_2$CH$_2$O)$_2$—A wherein A is an anionic metallacarborane cluster;

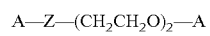

wherein M is Fe or Co;

wherein Z is —(OCH$_2$CH$_2$)$_2$—N$^+$H(R$^1$)—, —(OCH$_2$CH$_2$)$_2$—N$^+$(CH$_2$CH$_3$)$_2$—, —(OCH$_2$CH$_2$)$_2$—N(p-toluenesulfonyl)—, —(OCH$_2$CH$_2$)$_2$—X—, —N$^+$H$_2$— or —S—;

wherein $R^1$ represents hydrogen, $C_4$ alkyl, tert-butyl, 2-hydroxyethyl, benzyl, A, or —$(CH_2CH_2O)_2$—A, wherein X represents —O—, —CH($C_6H_5$)—CH($C_6H_5$)—, —OCH$_2$C(CH$_2$OCH$_2$C$_6$H$_5$)$_2$CH$_2$O—,

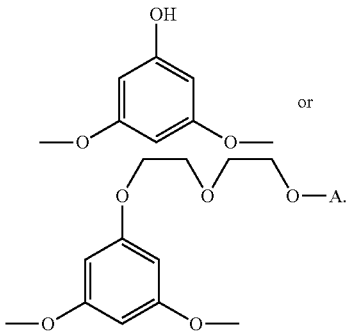

2. A HIV protease inhibitor composition comprising a compound of formula:

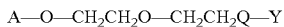

A—O—CH$_2$CH$_2$O—CH$_2$CH$_2$Q—Y wherein A is an anionic metallacarborane cluster

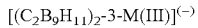

$[(C_2B_9H_{11})_2$-3-M(III)$]^{(-)}$ wherein M is Fe or Co, wherein Q is —O— or —NH—, wherein Y is —CH($C_6H_5$)—CH$_2$($C_6H_5$), —1-$C_6H_4$-4-CH$_2$-1-$C_6H_5$, —1-$C_6H_5$-C($C_6H_5$)$_3$, —1-$C_6F_5$, —CH$_2$C(CH$_2$OCH$_2$C$_6$ H$_5$)$_2$CH$_2$OH, —CH(CH$_2$C$_6$H$_5$)$_2$ or —1-$C_6H_4$-4-$C_2H_4$-$C_6H_5$, when Q is —O—, wherein Y is p-toluenesulfonyl, p-SO$_2$-C$_6$H$_4$-NH$_2$ or 1-SO$_2$-2,4,6-(CH$_3$)$_3$-$C_6H_3$, when Q is —NH—;

or

HIV protease inhibitor composition comprising a compound of formula:

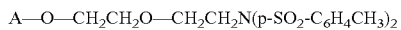

A—O—CH$_2$CH$_2$O—CH$_2$CH$_2$N(p-SO$_2$-C$_6$H$_4$CH$_3$)$_2$ wherein A is an anionic metallacarborane cluster

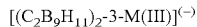

$[(C_2B_9H_{11})_2$-3-M(III)$]^{(-)}$ wherein M is Fe or Co.

3. A HIV protease inhibitor composition comprising a compound of formula:

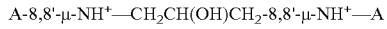

A-8,8'-µ-NH$^+$—CH$_2$CH(OH)CH$_2$-8,8'-µ-NH$^+$—A wherein A is an anionic metallacarborane cluster

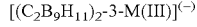

$[(C_2B_9H_{11})_2$-3-M(III)$]^{(-)}$ wherein M is Fe or Co.

* * * * *